(12) United States Patent
Cook et al.

(10) Patent No.: US 9,506,850 B2
(45) Date of Patent: Nov. 29, 2016

(54) APPARATUS AND METHOD FOR DETERMINING ONE OR MORE CHARACTERISTICS OF A VISCOUS MATERIAL

(71) Applicant: WesTech Engineering, Inc., Salt Lake City, UT (US)

(72) Inventors: Robert D. Cook, Salt Lake City, UT (US); Jerold L. Johnson, Holladay, UT (US); Philip Lake, Sandy, UT (US)

(73) Assignee: WesTech Engineering, Inc., Salt Lake City, UT (US)

( * ) Notice: Subject to any disclaimer, the term of this patent is extended or adjusted under 35 U.S.C. 154(b) by 237 days.

(21) Appl. No.: 14/270,221

(22) Filed: May 5, 2014

(65) Prior Publication Data

US 2014/0326054 A1 Nov. 6, 2014

Related U.S. Application Data

(60) Provisional application No. 61/819,738, filed on May 6, 2013.

(51) Int. Cl.
*G01N 11/14* (2006.01)

(52) U.S. Cl.
CPC ................... *G01N 11/14* (2013.01)

(58) Field of Classification Search
CPC . B01D 21/04; B01D 21/34; B01F 15/00246; G01N 11/14; G01N 33/383; G01N 2011/0046; G01N 11/10; G01N 11/00; G01N 2203/0025; G01N 2203/0092; G01N 33/343; G01N 9/26

See application file for complete search history.

(56) References Cited

U.S. PATENT DOCUMENTS 3,402,729 A * 9/1968 Richmond ............. G01N 11/14
137/92
3,812,706 A * 5/1974 Higgs .................... G01N 11/14
73/54.29

(Continued)

FOREIGN PATENT DOCUMENTS

DE 102010031857 * 1/2012
JP 02201122 A1 * 8/1990

(Continued)

OTHER PUBLICATIONS

English-language translation of DE 102010031857 A1 titled "Method and Apparatus for Measuring Sludge Levels" to Foerster et al. originally published on Jan. 26, 2012.*

(Continued)

*Primary Examiner* — David A Rogers
(74) *Attorney, Agent, or Firm* — Austin Rapp & Hardman

(57) ABSTRACT

The disclosed apparatus may include a mounting structure. A first arm may be secured to the mounting structure and may extend from the mounting structure. A load cell may be mechanically coupled to the first arm to detect a first load applied to the first arm by relative movement between the first load cell and a viscous material in which the first arm may be submerged or at least partially disposed. A second arm may be secured to the mounting structure and may extend from the mounting structure. A second load cell may be mechanically coupled to the second arm to detect a second load applied to the second arm by relative movement between the second load cell and the viscous material. In one embodiment, load data related to the first and second loads may be used to estimate or determine at least one characteristic of the viscous material.

19 Claims, 12 Drawing Sheets

(56) References Cited

U.S. PATENT DOCUMENTS

| | | | | |
|---|---|---|---|---|
| 4,332,158 A * | 6/1982 | Osborne | ................ | G01N 11/14 73/54.03 |
| 4,348,278 A | 9/1982 | Caccia | | |
| 4,637,417 A | 1/1987 | Schramm | | |
| 5,157,962 A * | 10/1992 | Fitzgerald | ............. | G01N 11/16 73/32 A |
| 5,357,785 A * | 10/1994 | Hemmings | ............... | B01L 9/00 73/54.32 |
| 5,684,247 A * | 11/1997 | Preikschat | ............ | G01N 11/14 73/53.03 |
| 6,481,267 B1 * | 11/2002 | Iles | ........................ | G01N 11/14 73/54.28 |
| 6,485,171 B1 | 11/2002 | Wang | | |
| 6,609,431 B1 | 8/2003 | Tietsworth et al. | | |
| 6,782,735 B2 * | 8/2004 | Walters | ................. | G01N 11/14 73/54.28 |
| 6,874,353 B2 * | 4/2005 | Johnson | ................. | G01N 11/14 73/54.28 |
| 6,878,280 B2 * | 4/2005 | McDowell | ............ | B01D 21/04 210/103 |
| 6,928,860 B1 * | 8/2005 | Hildebrandt | .............. | B01L 7/02 73/54.28 |
| 6,997,045 B2 * | 2/2006 | Wallevik | ................. | B01F 7/063 73/54.28 |
| 7,021,123 B2 * | 4/2006 | Wallevik | ................. | B01F 7/063 73/54.02 |
| 7,624,625 B2 * | 12/2009 | Jau | ........................ | G01N 11/14 366/142 |
| 7,712,526 B2 * | 5/2010 | Morgan | ................. | G01N 11/14 166/250.1 |
| 7,926,326 B2 * | 4/2011 | Franck | ................... | G01N 11/14 73/54.23 |
| 7,958,773 B2 * | 6/2011 | Dreisorner | ............ | G01N 33/10 73/54.28 |
| 7,992,427 B2 * | 8/2011 | Tonmukayakul | ....... | G01N 11/14 73/54.28 |
| 8,555,707 B2 * | 10/2013 | Dreisoerner | ........... | G01N 33/10 73/54.28 |
| 8,794,051 B2 * | 8/2014 | Morgan | ................. | G01N 11/14 73/54.01 |
| 9,274,038 B2 * | 3/2016 | Murphy | ................. | G01N 11/14 |
| 2001/0037673 A1 * | 11/2001 | Jackson | ................ | G01N 11/10 73/54.23 |
| 2005/0132782 A1 * | 6/2005 | Wallevik | ................. | B01F 7/063 73/54.28 |
| 2005/0138991 A1 * | 6/2005 | Wallevik | ................. | B01F 7/063 73/54.02 |
| 2005/0166667 A1 | 8/2005 | Hajduk et al. | | |
| 2006/0070428 A1 * | 4/2006 | Bateson | ................. | G01N 11/14 73/54.32 |
| 2008/0060423 A1 * | 3/2008 | Jau | ........................ | G01N 11/14 73/54.31 |
| 2008/0230220 A1 * | 9/2008 | Morgan | ................. | G01N 11/14 166/250.1 |
| 2010/0116032 A1 * | 5/2010 | Ruosaari | .............. | G01N 33/343 73/54.28 |
| 2010/0116033 A1 * | 5/2010 | Hoenderkamp | ....... | G01N 11/10 73/54.28 |
| 2010/0116034 A1 * | 5/2010 | Abbott | ................... | G01N 11/14 73/54.35 |
| 2010/0181070 A1 * | 7/2010 | Harris | ...................... | C09K 8/04 166/280.1 |
| 2011/0247402 A1 * | 10/2011 | Dreisorner | ............ | G01N 33/10 73/54.31 |
| 2012/0210774 A1 | 8/2012 | Raffer | | |
| 2014/0033803 A1 * | 2/2014 | Ozadali | .............. | B01F 7/00033 73/54.28 |
| 2014/0137638 A1 * | 5/2014 | Liberzon | ................ | G01N 11/14 73/54.28 |

FOREIGN PATENT DOCUMENTS

| | | |
|---|---|---|
| WO | WO9600885 | 1/1996 |
| WO | WO9721988 | 6/1997 |
| WO | WO0116591 | 3/2001 |
| WO | 2013001538 | 1/2013 |
| WO | WO2013001538 | 1/2013 |
| WO | WO2013171652 | 11/2013 |

OTHER PUBLICATIONS

PCT/US2014/37034, International Preliminary Report on Patentability, mailed on Nov. 19, 2015.
International Search Report for International Application No. PCT/US2014/37034, Sep. 30, 2014.
Written Opinion for International Application No. PCT/US2014/37034, Sep. 30, 2014.
Eagle Iron Works, Classifying Equipment, Electronic Brochure, published in 2004 based on the associated URL (Attachment A).
Eagle Iron Works, Classifying Tanks, Electronic Brochure, Eagle Iron Works, published in 2003 (Attachment B).
Royce Technologies, Interface Level Analyzer and Sensors, Electronic Brochure, published in Dec. 2006 (Attachment C).
Royce Technologies, SmartDiver—Automatic Mud-Diver & Interface Detection System for Thickeners & CCD's, Web page, published at least by Oct. 14, 2009 according to archive.org (Attachment D).
Precision Light & Air Pty Ltd., SmartDiver—Level Measurement & Analyzer System—Smart Diver Compact & Smart Diver 'Duo', Electronic Brochure, published at least by Oct. 14, 2009 according to archive.org (Attachment E).
Precision Light & Air Pty Ltd., SmartDiver—Automatic Mud-Diver & Interface Detection System for Thickeners & CCD's, Web page, published at least by Aug. 28, 2009 according to archive.org (Attachment F).

* cited by examiner

APPARATUS AND METHOD FOR DETERMINING ONE OR MORE CHARACTERISTICS OF A VISCOUS MATERIAL

RELATED APPLICATIONS

This application claims priority to and is a non-provisional application of U.S. Provisional Application Ser. No. 61/819,738 filed on May 6, 2013, which is incorporated herein by this reference.

TECHNICAL FIELD

The present invention relates generally to an apparatus and a method for ascertaining one or more characteristics of a viscous material.

BACKGROUND

A thickener or other apparatus may be used in the field of gravity-driven separation of a solid-liquid mixture (a viscous material) into clarified liquid and concentrated solids. Feed may enter a thickener in a feedwell, for example, at the center of the thickener where a reagent (e.g., a flocculant) is added to enhance separation. In steady state operation of such a thickener, three distinct zones are formed with the processed viscous material. The upper zone contains clarified liquid. Below that is a settling zone where solid particles are moving generally downward while liquid is moving generally upward. The lowest is the compaction zone. Usually the interface between the settling zone and compaction zone is quite distinct, having different physical properties.

There have been several methods introduced in the industry to locate this interface, or bed location, within the thickener. These methods include ultrasonic sensors mounted on the bridge and a differential pressure sensor mounted on the bottom of the tank. These methods infer the bed location indirectly rather than directly. Further, consistent identification of the bed level on a continuous basis in the dynamic thickening process has proven difficult using these methods. In addition, the effectiveness of the flocculants, which are often used in thickeners, results in evolving density gradients clouding the interface and creating a fluffy bed, which often results in bed level measurement errors.

Another method employed in the industry mechanically lowers a conductivity sensor down from the bridge into the thickener, measuring the conductivity profile as it is lowered. The expense of this method and the chance of entanglement with a raking mechanism, which is often used in a thickener, are additional drawbacks for this method. Further, this method does not continuously obtain data regarding the state of the viscous material within the thickener.

Furthermore, problems can arise in the thickener because of variations in the horizontal gradient of the viscous material. Without this knowledge, an operator of the thickener may improperly add or reduce, for example, flocculant to the viscous material, potentially exacerbating the problem.

Accordingly, an improved apparatus for ascertaining an interface between the compaction zone and the settling zone in a viscous material within a thickener is desirable. An improved apparatus for ascertaining the horizontal viscosity characteristics of a viscous material within a thickener is also desirable.

SUMMARY

Embodiments of the disclosed subject matter are provided below for illustrative purposes and are in no way limiting of the claimed subject matter.

An apparatus for sensing differences in viscosity within a viscous material is disclosed. The apparatus may include a member mechanically configured to rotate, and a first arm may be secured to the member mechanically configured to rotate and may extend from the member mechanically configured to rotate. A first load cell may be mechanically coupled to the first arm to detect a first load applied to the first arm and to produce first load data indicative of the first load.

A second arm may be secured to the member mechanically configured to rotate and may extend from the member mechanically configured to rotate. The second arm may be offset from the first arm. A second load cell may be mechanically coupled to the second arm to detect a second load applied to the second arm and to produce second load data indicative of the second load.

A data analysis device may be electrically coupled to the first load cell and to the second load cell. The data analysis device may be configured to receive the first load data and second load data and to analyze differences between the first load data and the second load data to generate at least one estimate of a characteristic of the viscous material when at least one of the first and second arms is submerged within or at least partially disposed in the viscous material.

The first and second arms may comprise a first probe and a second probe, respectively. The first and second probes may be oriented generally perpendicular to a direction along which the first and second probes move through the viscous material in response to rotation of the first and second arms. The first and second probes may be mechanically coupled to the first and second load cells to transmit force to the first and second load cells in proportion to fluid drag on the first and second probes.

The first and second load cells may each be selected from the group consisting of strain gauges, pressure detectors, piezoelectric load cells, vibrating wire load cells, and capacitive load cells.

The first load cell may comprise a first strain gauge secured to the first arm to measure strain of the first arm incident to fluid drag induced by motion of the first arm through the viscous material when the first arm is submerged within the viscous material. The second load cell may comprise a second strain gauge secured to the second arm to measure strain of the second arm incident to fluid drag induced by motion of the second arm through the viscous material when the second arm is submerged within the viscous material.

The member mechanically configured to rotate may comprise an axial dimension parallel to an axis of rotation of the member mechanically configured to rotate and a radial dimension perpendicular to the axial dimension. The first arm may be offset from the second arm along the radial dimension, along the axial dimension or along both the radial and the axial dimensions.

The apparatus may further comprise a third arm secured to the member mechanically configured to rotate and may extend outward from the member mechanically configured to rotate. The third arm may be offset from the second arm along the radial dimension, axial dimension, or along both of these dimensions. A third load cell may be mechanically coupled to the third arm to detect a third load applied to the third arm. A fourth arm may be secured to the member mechanically configured to rotate and may extend outward from the member mechanically configured to rotate. The fourth arm may be offset from the first arm along the radial dimension, axial dimension, or along both of these dimensions. A fourth load cell may be mechanically coupled to the fourth arm to detect a fourth load applied to the fourth arm.

The apparatus may further comprise a rake extending from the member mechanically configured to rotate for raking the viscous material. The apparatus may also comprise a gravity-driven sedimentation vessel shaped to hold the viscous material. The member mechanically configured to rotate may extend into the gravity-driven sedimentation vessel such that the rake is at least partially submerged in the viscous material when the viscous material is disposed within the gravity-driven sedimentation vessel.

One embodiment of the apparatus may also include a second member mechanically configured to rotate and a rake extending from the second member mechanically configured to rotate for raking the viscous material when the viscous material is disposed within the gravity-driven sedimentation vessel. The second member mechanically configured to rotate may be offset from the member mechanically configured to rotate.

The viscous material may comprise at least one viscosity gradient. The data analysis device may be configured to ascertain changes in the viscosity gradient based on the first load data and the second load data.

The data analysis device may be configured for electrical coupling to at least one process control device. The data analysis device may also be configured to generate process control data for the process control device based on the at least one estimate. The process control data may comprise an instruction for controlling an operation involving the viscous material. The data analysis device may be coupled to the at least one process control device through a wireless communication link.

Also, the data analysis device may be electrically coupled to at least one of the first load cell and the second load cell through a wireless communication link.

The apparatus may further comprise a gravity-driven sedimentation vessel shaped to receive an incoming slurry. The gravity-driven sedimentation vessel may be shaped to hold the viscous material. The viscous material may comprise at least a clarified liquid zone, a settling zone and a concentrated solids zone. The viscous material may comprise a vertical dimension, and the data analysis device may be configured to ascertain an estimate of a location of an interface between the settling zone and the concentrated solids zone along the vertical dimension based on the first load data and the second load data.

In one embodiment, an apparatus for sensing differences in viscosity within a viscous material may comprise a member mechanically configured to rotate. A first arm may be secured to the member mechanically configured to rotate and may extend from the member mechanically configured to rotate. A first load cell may be mechanically coupled to the first arm to detect a first load applied to the first arm by relative movement between the first load cell and the viscous material. A second arm may be secured to the member mechanically configured to rotate and may extend from the member mechanically configured to rotate, the second arm being offset from the first arm. A second load cell may be mechanically coupled to the second arm to detect a second load applied to the second arm by relative movement between the second load cell and the viscous material.

The member mechanically configured to rotate may comprise an axial dimension parallel to an axis of rotation of the member mechanically configured to rotate and a radial dimension perpendicular to the axial dimension. The first arm may be offset from the second arm along the axial dimension, the radial dimension, or along both the axial and the radial dimensions.

In one embodiment, an apparatus for sensing the viscosity of a viscous material is disclosed. The apparatus may sense viscosity of the viscous material within a gravity-driven sedimentation vessel shaped to hold the viscous material. The viscous material may have at least a clarified liquid zone near a top of the viscous material from which clarified water can be removed, and a concentrated solids zone near a bottom of the viscous material from which the concentrated solids can be removed. The concentrated solids zone may comprise a first viscosity. A settling zone containing settling solids may be located between the clarified zone and the concentrated solids zone. The settling zone may comprise a second viscosity different from the first viscosity. The apparatus may comprise a member mechanically configured to rotate extending into the viscous material. The apparatus may also comprise an arm secured to the member mechanically configured to rotate. A load cell may be mechanically coupled to the arm to detect a load applied to the arm by relative movement between the load cell and the viscous material in at least one of the clarified liquid zone, the concentrated solids zone, and the settling zone and to produce load data indicative of the load when the arm is at least partially disposed within the viscous material.

A data analysis device may be electrically coupled to the load cell. The data analysis device may be configured to receive the load data. The data analysis device may be configured to ascertain a location of an interface between the settling zone and the concentrated solids zone along a vertical dimension of the member mechanically configured to rotate based on the load data.

Methods associated with the foregoing apparatuses are also disclosed.

BRIEF DESCRIPTION OF DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

Figure 1:
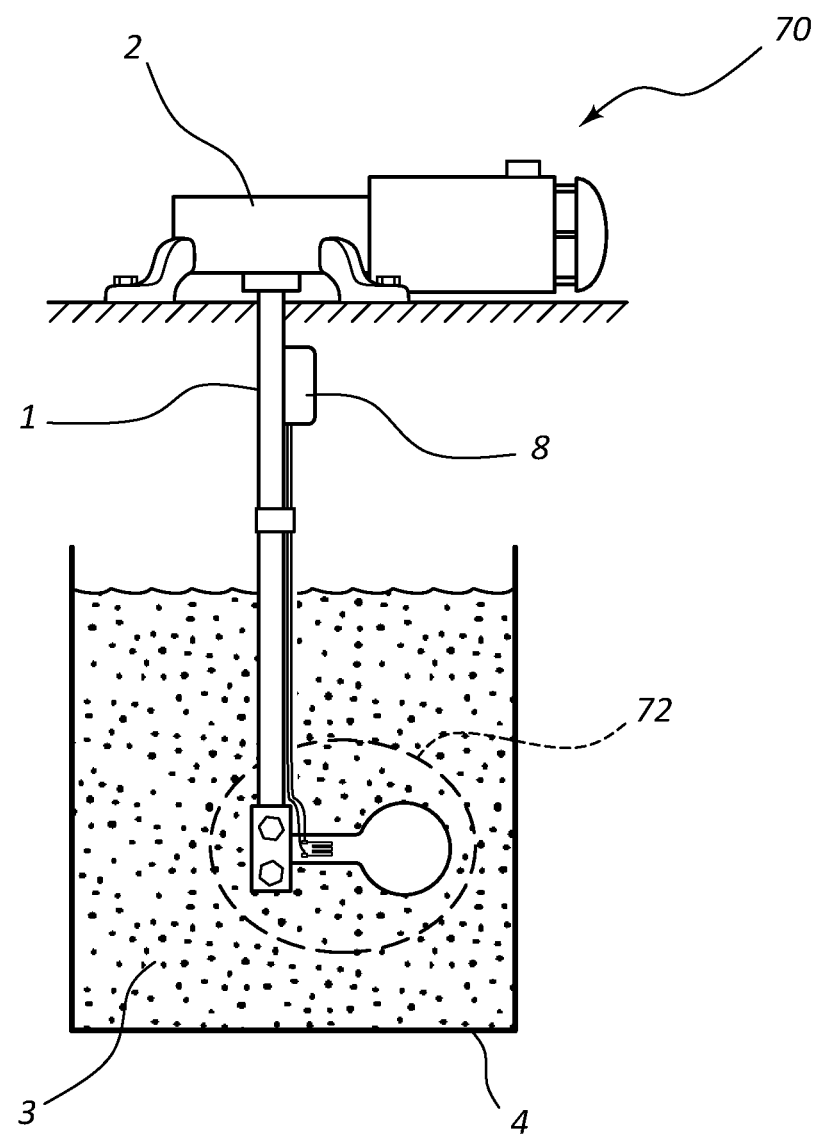
FIG. 1 is a side elevation, section view of an apparatus according to one embodiment of the invention, in which a sensor is attached to a shaft mechanically configured to rotate that extends into a container of viscous material to measure rheology of the viscous material.

In accordance with common practice, the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus (e.g., device) or method. Finally, like reference numerals may be used to denote like features throughout the specification and figures.

DETAILED DESCRIPTION

Various aspects of the disclosure are described below. It should be apparent that the teachings herein may be embodied in a wide variety of forms and that any specific structure, function, or both being disclosed herein is merely representative. Based on the teachings herein, one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein. Furthermore, an aspect may comprise at least one element of a claim.

The word "exemplary" is used exclusively herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The disclosed subject matter may be used, for example, to monitor the operation of a thickener or other apparatus in the field of gravity separation of a liquid-solid mixture into clarified liquid and concentrated solids. Feed (a viscous material) may enter a thickener in a feedwell, for example, at the center of the thickener where a reagent (e.g., a flocculant) is added to enhance separation. Clarified liquid commonly referred to as overflow may be withdrawn from the thickener in a launder near the top of a tank wall. Concentrated solids, or underflow, collect in the lower part of the tank and are usually withdrawn near the bottom center of the tank. Since solids will settle over the entire area of the thickener, a raking mechanism may be used. The raking mechanism rotates within the tank for the purpose of moving settled solids to the center where settled solids are discharged.

There are varieties of thickeners having specialized capabilities that are tailored to specific process needs of individual plants. One of the differentiating aspects of many thickeners is the depth of the mud bed that the thickeners are designed to achieve. This is an important aspect in the operation of a thickener because, in general, the longer the solids are in a thickener, the more concentrated they become. As the residence time of solids in the thickener changes, the concentration of the underflow and the rheological properties (e.g., viscosity and yield stress) changes as well. As a result, knowing the location of the settled solids inside a thickener is important to the proper operation of the thickener in order to achieve the desired underflow properties. Furthermore, the location of the bed level in relationship to the feedwell can significantly affect the clarity of the overflow. As a result, monitoring and controlling the bed level may help to provide an overflow clarity target.

In steady state operation, three distinct zones are formed inside the thickener. The upper zone contains clarified liquid. Below that is a settling zone where solid particles are moving generally downward while liquid is moving generally upward. The lowest is the compaction zone. Usually the interface between the settling zone and compaction zone is quite distinct, having different physical properties. There are several methods introduced into the industry to locate this bed level within the thickener. These methods include ultrasonic sensors mounted on the bridge and a differential pressure sensor mounted on the bottom of the tank. These methods infer the bed location indirectly. Consistent identification of the bed level on a continuous basis in the dynamic thickening process has proven difficult for these methods. The effectiveness of the flocculation of the solids results in evolving density gradients clouding the interface and creating a fluffy bed which results in bed level measurement errors.

Another method employed in the industry mechanically lowers a conductivity sensor down from the bridge into the thickener, measuring the conductivity profile as it is lowered. The expense of this method and the chance of entanglement with a raking mechanism are additional drawbacks for this method. The subject matter of this application provides an improved apparatus and method for locating the interface between settling and compaction zones.

Thickeners can also be prone to upsets that are difficult to diagnose. With only general signs such as poor underflow density and mechanism drive torque spikes to indicate that there is a problem, the operator may not know the cause of the problem. For example, the operator might conclude that low underflow density is a result of low flocculant dosage and therefore increase the dosage. But, the actual cause may be the formation of an "island" resulting from over flocculation, and the operator's action only aggravates the problem.

Many upset conditions can result in horizontal viscosity variations within the mud bed similar to the vertical variations that are seen during normal settling. The apparatus and method of the present application, in some embodiments, can detect these horizontal variations, in addition to or in the alternative to the vertical variations, providing the ability to understand the cause of these upset conditions and what corrective action is needed. This is a valuable improvement to the ability to operate and control thickeners to achieve optimum performance.

The apparatus and method of the application may more than just detect the bed level interface, but may also include the ability to provide data from within the mud bed that is proportional to the rheology (viscosity) at the point of measurement. Unlike instruments that measure hydrostatic head, electrical conductivity or reflected ultrasonic waves to sense bed level, the disclosed method and apparatus may provide direct data indicating whether the mud bed is acceptable for downstream processes when located near the discharge. Many downstream processes from the thickener (such as pumping, disposal of the solids, or further processing) depend on the thickener to produce underflow within a target viscosity range.

Referring to FIG. 1, a side elevation, section view illustrates an apparatus 70 according to one embodiment of the invention, in which a sensor 72 is attached to a shaft 1 that extends into a container 4 shaped to hold a viscous material 3. The shaft 1 (which may also be referred to as a member mechanically configured to rotate 1) may rotate, and may be used only for the sensor 72, or may have one or more additional functions, such as the rotation of a rake that facilitates a settling and/or separation process carried out on the viscous material 3. The sensor 72 may be used to measure rheology of the viscous material 3, which may include, but is not limited to, the viscosity of the viscous material 3 at one or more locations within the viscous material 3. The shaft 1 may be rotated, for example, through the use of a motor 2, which may be an electric powered gear motor or the like, and may be positioned outside or inside the container 4. The shaft 1 may have a proximal end coupled to the motor 2, and a distal end that extends into the viscous material 3 within the interior of the container 4.

The container 4 of the apparatus 70 may, in one embodiment, be a settling tank. More precisely, the container 4 may be a gravity-driven sedimentation vessel or the like. The present invention may be used in conjunction with a wide variety of viscous fluids and containment and/or processing systems. The shape of the container 4 in FIG. 1 is merely exemplary. A wide variety of container shapes may be used within the scope of the present invention. Other exemplary container shapes will be shown and described in connection with FIGS. 9A-10B.

Figure 2A:
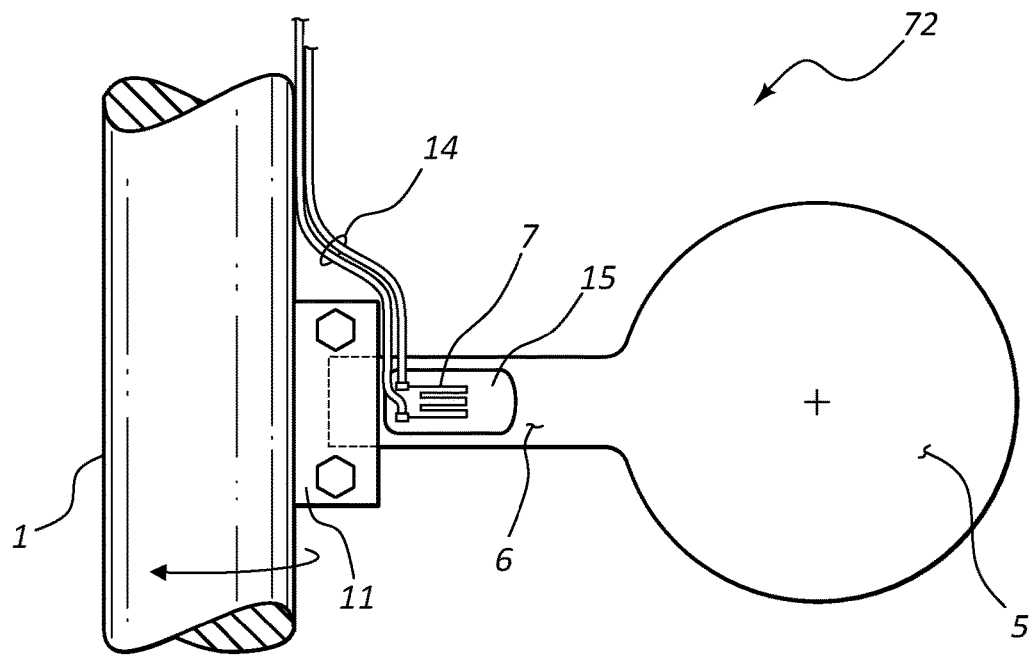
FIG. 2A is a side elevation view of the sensor of FIG. 1.
Figure 2B:
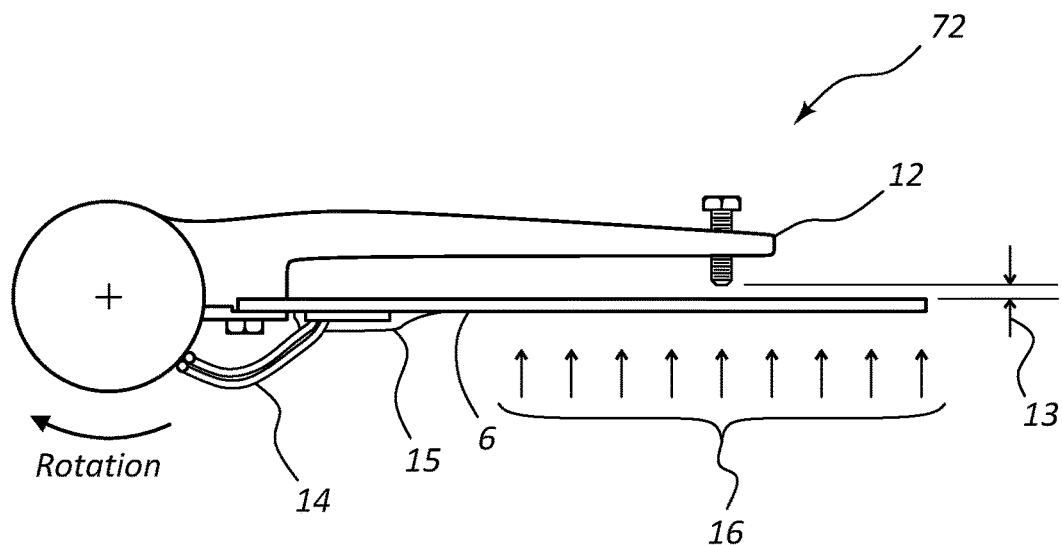
FIG. 2B is a top view of the sensor of FIG. 1.

Referring to FIGS. 2A and 2B, a side elevation view and a top view, respectively, illustrate the sensor 72 of FIG. 1 in greater detail. As shown, the sensor 72 may include a probe 5 having a convenient geometry with a frontal area so that the viscous pressure 16 created as the probe 5 moves through the viscous material 3 causes a resulting force on the probe. The probe 5 may be positioned at the end of an arm 6. The viscous pressure 16 may be created incident to fluid drag force on the probe 5. The fluid drag force, and thus the viscous pressure 16, may increase with greater viscosity of the viscous material 3.

The viscous pressure 16, and thence, the viscosity of the viscous material 3, may be detected through the use of a load cell. A "load cell" includes any of a wide variety of sensor devices that detect a load (i.e., a force), whether the force is generated by a point loading, fluid pressure, or any other source. A load cell can include any of a wide variety of sensor types, including but not limited to strain gauges, pressure detectors, piezoelectric load cells, vibrating wire load cells, and capacitive load cells. Any of the foregoing may be used in conjunction with a member moving through a viscous material to evaluate the viscosity of the viscous material.

In FIGS. 2A and 2B, the sensor 72 may utilize a load cell in the form of a strain gauge 7. More precisely, the viscous pressure 16 may urge the probe 5 upward, relative to the view of FIG. 2B, which force may result in a deflection of the arm 6. This deflection results in strain in the arm 6, which may be detected through the use of a load cell in the form of one or more strain gauges 7 secured to the arm 6. If more than one of the strain gauges 7 are used, they may be arranged in an electrical bridge circuit such as a Wheatstone bridge. The strain gauges 7 may, in one embodiment, advantageously be positioned toward the proximal end of the arm 6 (the end of the arm 6 that is secured to the shaft 1) because the bending moment, and hence the strain in the arm 6, will be greater at the proximal end. Thus, the sensitivity of the strain gauges 7 may be increased by placing them nearer the shaft 1. The geometry of the probe 5 in this embodiment may be generally circular, providing similar physical properties in all directions and a shape that is easily fabricated. Other probe geometries (such as square, rectangular, octagonal, hexagonal or oval shapes) may be used within the scope of the invention.

The strain gauges 7 may be connected to a wireless transceiver 8 (shown in FIG. 1) by electrical wires 14. The wireless transceiver 8 may be located out of the viscous material 3 so that the viscous material 3 will not interfere with the operation of the wireless transceiver 8. The wireless transceiver 8 may be powered, for example, by an internal, rechargeable battery or through a connection to a power grid or another power source, and may be positioned at any suitable location relative to the sensor 72. As shown, the wireless transceiver 8 may be attached to the shaft 1 above the surface of the viscous material 3. A wireless transceiver 9 (shown in FIG. 4) may be located in the general vicinity of the wireless transceiver 8, and may be connected to a data analysis device 10 (also shown in FIG. 4), which may collect load data 62 (also shown in FIG. 4) transmitted by the wireless transceiver 8. The data analysis device 10 may store the load data and/or use it for calculations and/or control of other process functions related to processing of the viscous material 3.

As shown in FIG. 2A, the sensor 72 of FIG. 1 may be attached to the shaft 1 by a clamping device 11, which may facilitate assembly and/or maintenance of the sensor 72. As shown in FIG. 2B, an overload protection device 12 may be part of the structure of the shaft 1, or may be a separate piece attachable to the shaft 1 through the use of one or more fasteners and/or other attachment devices. The overload protection device 12 may limit deflection of the probe 5 and arm 6, thus helping to prevent damage to the sensor 72 in the event that the sensor 72 is subjected to excessive stress, for example, due to a sudden increase in the viscous pressure 16. The gap 13 between the overload protection device 12 and the probe 5 may be adjustable to permit alteration of the level of strain experienced by the arm 6 before the overload protection device 12 begins limiting further strain. This adjustment may be carried out, for example, by rotating a set screw, shown in FIG. 2B, to increase or decrease the size of the gap 13.

In some implementations, the viscous material 3, in which the sensor 72 operates, may be a mixture of liquid and solid materials. The strain gauges 7 and electrical wires 14, if exposed to and moving through such material, may experience mechanical wear and generate inaccurate signals due to electrical conductivity between these items and the viscous material 3. Thus, as embodied in FIGS. 2A and 2B, the sensor 72 may have a protective coating 15 used to isolate these components mechanically and/or electrically from contact with the viscous material 3. This protective coating 15 can be an elastomeric material attached to the surface of at least the strain gauges 7 and wiring connections used to secure the electrical wires 14 to the sensor 72. Alternatively or additionally, the protective coating 15 may be applied to the electrical wires 14 and/or to the entire sensor 72. The material of which the protective coating 15 is formed may allow the sensor 72 to move the small amounts necessary for measurement purposes while causing minimal changes to the output signal. Protection of the sensor 72 may also be accomplished by encasing the sensor 72 in a thin elastomeric membrane or by placing the sensor 72 inside a waterproof housing.

Figure 3A:
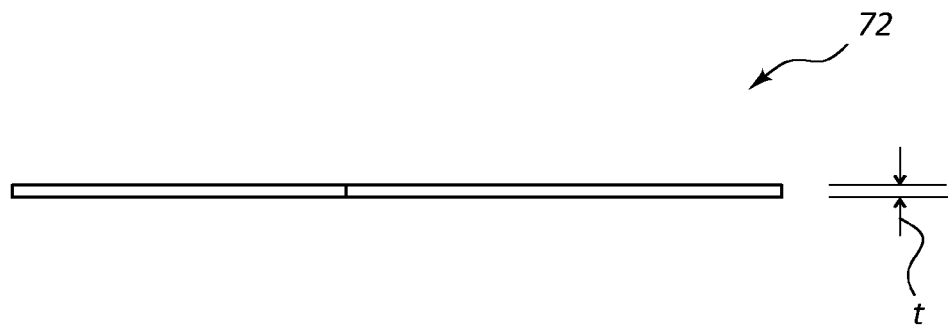
FIG. 3A is a top view of the sensor of FIG. 1, showing the thickness of the arm of the sensor.
Figure 3B:
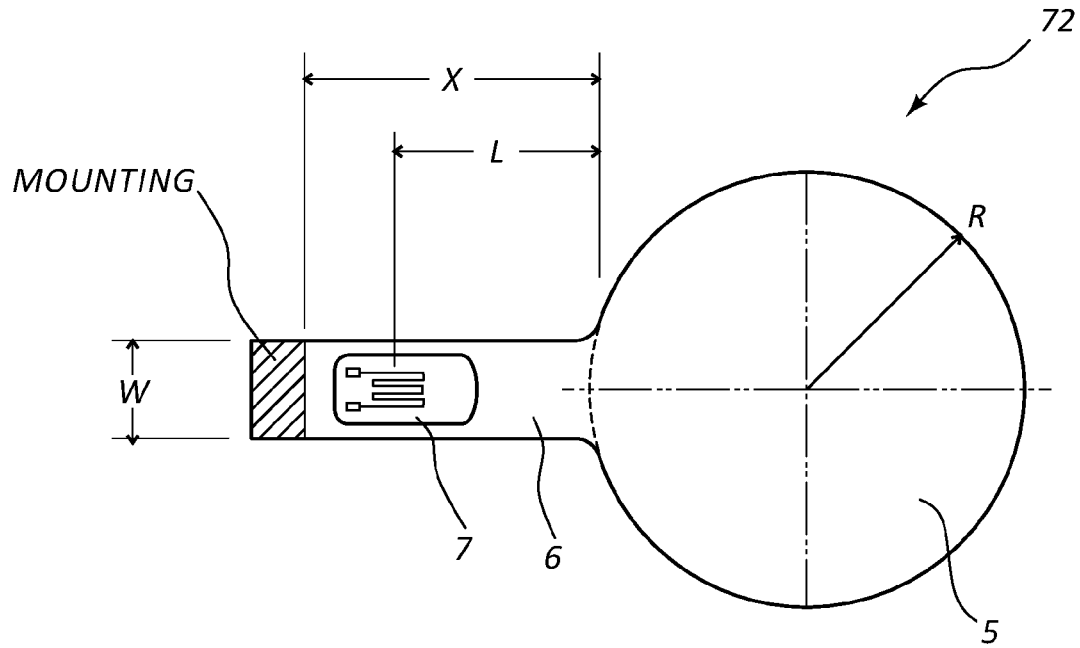
FIG. 3B is a side elevation view of the sensor of FIG. 1, showing the geometry of the arm of the sensor in greater detail.

Referring to FIGS. 3A and 3B, a top view and a side elevation view, respectively, illustrate the sensor of FIG. 1, showing the thickness and geometry of the sensor 72 in greater detail. This embodiment of the sensor 72 was tested with geometry as follows: R=1.25 inches, X=1.50 inches, L=0.75 inches, W=0.50 inches, and t=0.012 inches. This exemplary geometry provided easily measured output signals from the strain gauges 7 for the range of rheological properties of interest for a tested viscous material 3. Different geometries of the probe 5 and/or the arm 6 may make it possible to obtain sensors that are more or less sensitive than the exemplary embodiment of FIGS. 3A and 3B. For example, a larger diameter probe 5 or a longer arm 6 may provide a larger output signal than that of the sensor 72 as dimensioned in FIGS. 3A and 3B. In this way, output characteristics of the sensor 72 can be adjusted to suit the viscosity range, and thence the viscous pressure range, expected from different viscous materials 3.

The sensor 72 illustrated in FIGS. 1-3B was tested in several different viscous materials. One material in which the sensor 72 was tested was mine tailings. Tests were conducted at 5 different tailings concentrations plus water. These concentrations, the resulting viscosities and the associated sensor output signals are reported in Table 1, which is provided below. Knowing the sensor geometry, the output signal data (in units of micro-strain) can be converted to units of pressure or force on the probe 5. The pressure or force can, in turn, be used to determine viscosity.

TABLE 1

| Test Number | Solids Concentration wt % | Yield Stress Pa | Bingham Viscosity Pa · s | Sensor Signal Micro-Strain |
|---|---|---|---|---|
| 1 | 72.1 | 225 | 3.54 | 2240 |
| 2 | 69.9 | 145 | 2.34 | 1340 |
| 3 | 68.5 | 108 | 1.78 | 1140 |
| 4 | 67.8 | 80 | 1.36 | 740 |
| 5 | 66.1 | 40 | 0.75 | 380 |
| 6 (water) | 0 | 0 | 0 | <6 |

TABLE 1-continued

The sensor output signal is dependent on the geometry of the sensor 72, the velocity of the sensor 72 relative to the viscous material 3, and the rheology of the viscous material 3. Test data demonstrates that for any single sensor 72 and velocity, the output signal and viscosity relationship is generally linear within the range of interest.

Figure 4:
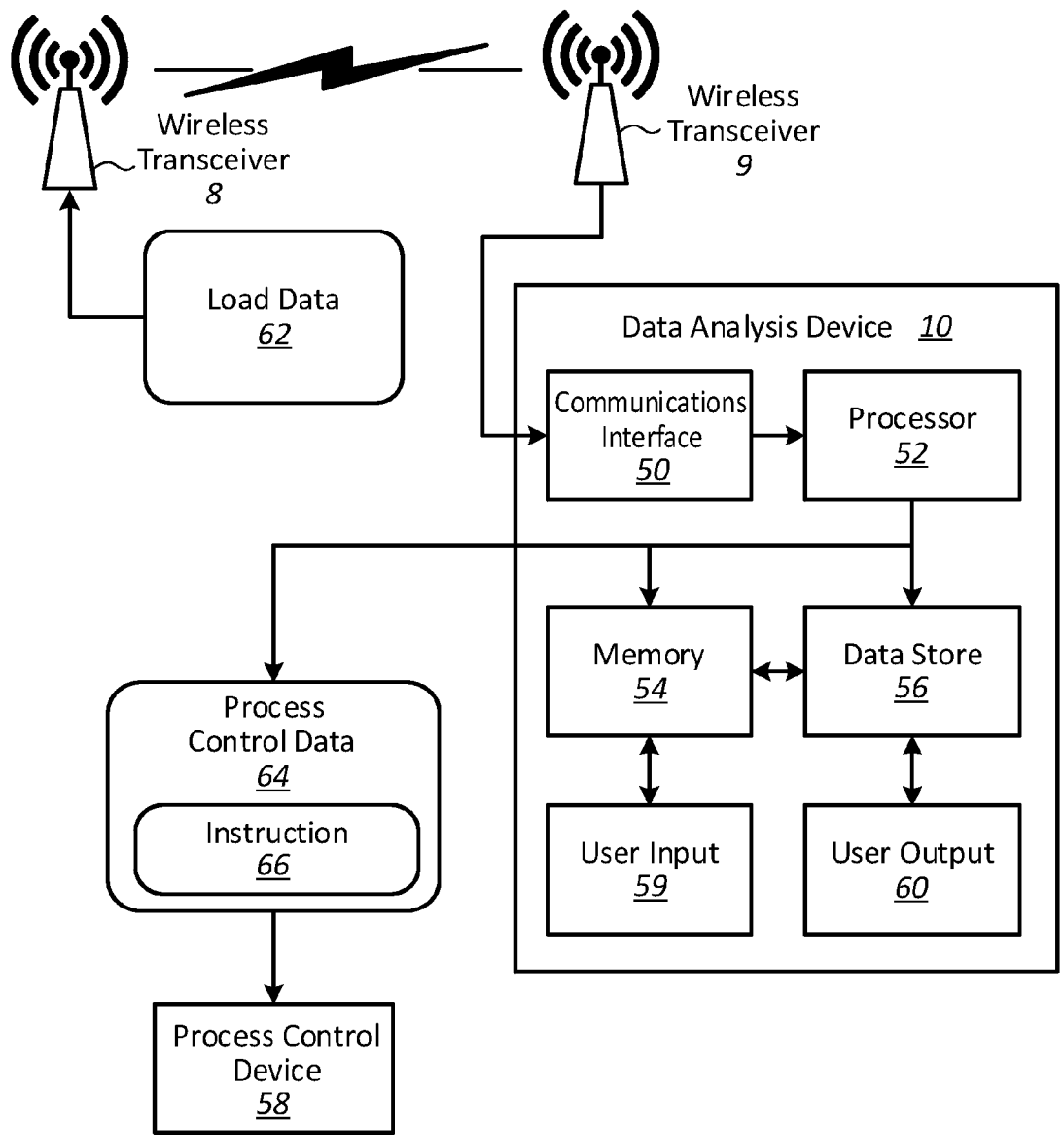
FIG. 4 is a schematic block diagram illustrating the wireless transceiver of FIG. 1, along with a data analysis device that receives load data from the wireless transceiver and transmits process control data to a process control device.

Referring to FIG. 4, a schematic block diagram illustrates the wireless transceiver 8 of FIG. 1, along with a data analysis device 10 that receives load data 62 from the wireless transceiver 8 and transmits process control data 64 to a process control device 58 via a wired or wireless communication link to the process control device 58. As described previously, the wireless transceiver 8 may be connected to the strain gauges 7 via the electrical wires 14, and may receive load data 62 from the strain gauges 7. The wireless transceiver 8 may wirelessly transmit the load data 62 to a wireless transceiver 9 connected to the data analysis device 10. In an alternative embodiment, load data 62 may be communicated to the data analysis device 10 via a physical (rather than wireless) connection.

The data analysis device 10 may be, for example, a computer, smartphone, tablet or a dedicated device. In some embodiments, the data analysis device 10 may include components, such as a communications interface 50, a processor 52, a memory 54, a data store 56, a user input 59, and a user output 60. The communications interface 50 may enable wireless and/or wired communication with the data analysis device 10. The communications interface 50 may utilize various antennas and/or connectors, such as USB connectors, Ethernet connectors, Wi-Fi radio frequency antennas, and the like to connect to other devices. As shown, the communications interface 50 may be connected to the wireless transceiver 9 so that the data analysis device 10 can receive the load data 62 from the wireless transceiver 9 via the communications interface 50.

The processor 52 may be of any known type, including but not limited to microprocessors, application-specific integrated circuits (ASICs), field-programmable gate arrays (FPGA's), and the like. The memory 54 may be volatile memory that stores operating instructions, load data 62, analysis results, process control data 64 and/or other data related to the operation of the data analysis device 10. The data store 56 may have non-volatile memory that stores computer program code and/or other data (e.g., load data 62 and analysis results) pertinent to the operation of the data analysis device 10. Programming code for the data analysis device 10 may comprise, for example, embedded or non-embedded software for programming code. The user input 59 and/or the user output 60 may optionally enable a user to communicate with the data analysis device 10. Such communication may be useful to activate, deactivate, and/or modify the operating settings of the data analysis device 10, wireless transceiver 8 and/or sensors 72.

The communications interface 50, the processor 52, the memory 54, the data store 56, the user input 59, and/or the user output 60 may communicate with each other via a system bus (not shown) or the similar communication mechanisms, systems or protocols. Additionally or alternatively, the data analysis device 10 may be connected via a wired or wireless connection to the process control device 58. The process control device 58 may be a controller that controls one or more aspects of the operation of the apparatus 70. For example, the process control device 58 may control the rate of ingress of the viscous material 3 into the container 4, the rate of outflow of liquid and/or solid material, the rate at which a rake or other stirring device operates, the rate at which flocculant is added to the viscous material 3, and/or other factors. The process control device 58 may be designed to operate with or without human intervention.

The data analysis device 10 may receive the load data 62 and, based on the load data 62, formulate an estimate of one or more properties or characteristics of the viscous material 3. The characteristic may be a viscosity level, a consistency level, a height of an interface between the adjacent zones within the viscous material 3, or the like. Estimating the one or more characteristic may enable the data analysis device 10 to provide the process control data 64 to the process control device 58. The process control data 64 may, for example, include an instruction 66 regarding an action to be taken (or avoided) by the process control device. The instruction 66 may be determined based on the results of analysis of the load data 62 by the data analysis device 10.

In alternative embodiments, the various components and/or functions described above may be divided differently between the data analysis device 10 and the process control device 58. In some embodiments, the data analysis device 10 may be combined with the process control device 58 so that one single device carries out analysis and control functions. Further, although the apparatus 70 includes a mixture of wireless and wired communications, wired or wireless communications of any known protocol and any known stages may be used to convey data from the sensor 72 to the data analysis device 10 and/or convey data from the data analysis device 10 to the process control device 58.

Figure 5:
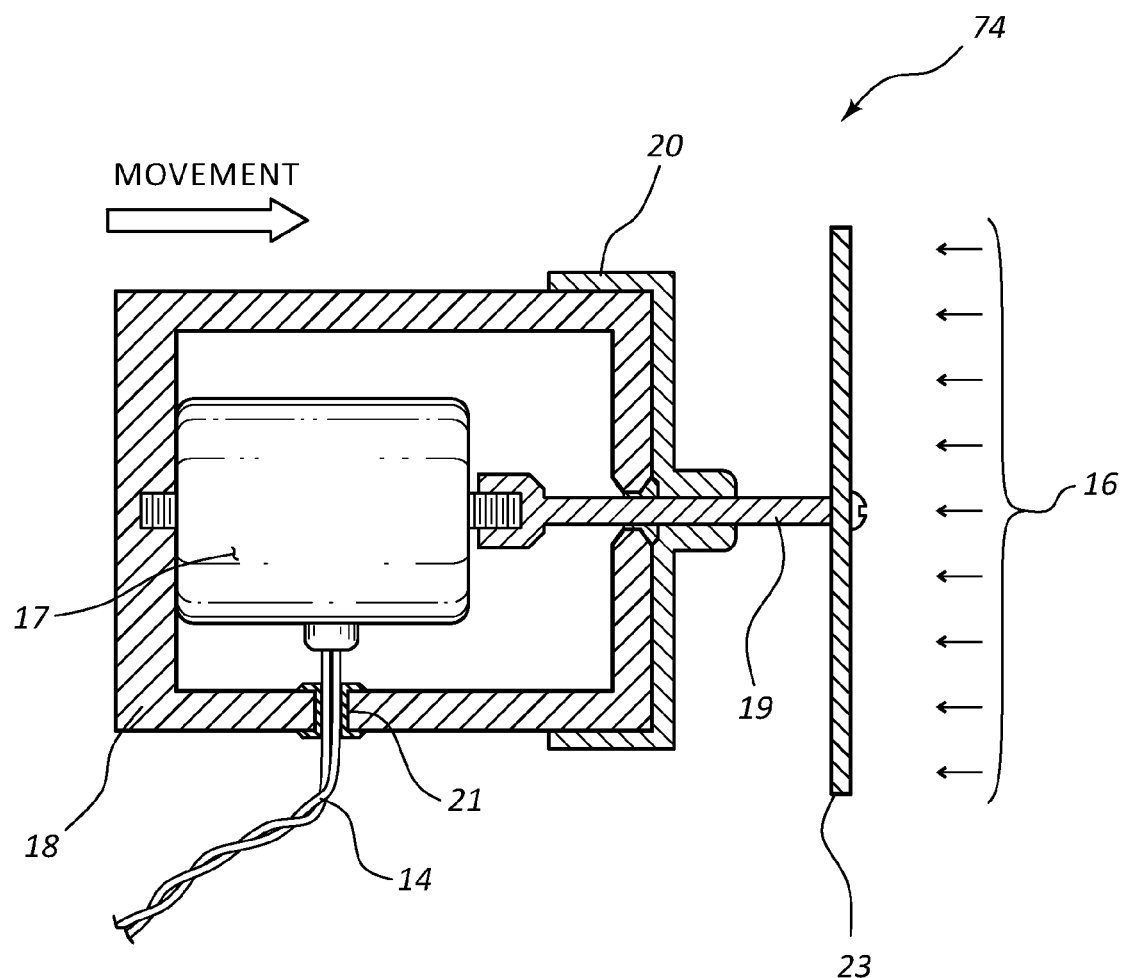
FIG. 5 is a side elevation, section view of a sensor according to another embodiment of the invention, with a load cell enclosed in a protective housing.

Referring to FIG. 5, a side elevation, section view illustrates a sensor 74 according to another embodiment of the invention. In the embodiment of FIG. 5, the force exerted by the viscous pressure 16 on a probe 23 may be measured by a load cell 17 mounted in a protective housing 18 that is sectioned in FIG. 5 to make the load cell 17 visible. The sensor 74 can be submerged in and/or moved through the viscous material 3 in a manner similar to that of the previous embodiment or by other methods. Thus, the sensor 74 may, if desired, also be secured to the end of an arm that rotates, like the arm 6 of FIGS. 1-3B.

In this embodiment, force from the probe 23 acts on the load cell 17, through a shaft 19. As illustrated in FIG. 5, the entire load cell 17 may be protected from the viscous material 3 by a protective housing 18 and by an elastomeric membrane 20 that provides a flexible joint between the protective housing 18 and the shaft 19. The protective housing 18 and the joint provided by the elastomeric membrane 20 may both be watertight. Electrical wires 14 may communicate load data 62 from the load cell 17 to the wireless transceiver 8. The opening 21 where the electrical wires 14 go through the protective housing 18 may be made watertight by filling it with a commercially available potting compound that adheres to the protective housing 18 and to the electrical wires 14.

The load cell 17 may also be a strain gauge. If desired, the load cell 17 may contain one or more elements that deflect in response to the force exerted on the load cell 17 by the viscous pressure 16 through the probe 23. Alternatively, the load cell 17 may be a different type of load cell, such as a piezoelectric load cell. Notably, some load cell types, such as piezoelectric load cells, may measure the change in load, rather than a static load. For such load cell types, the data analysis device 10 may be configured to derive the static load from load data 62 based on changes to the load experienced by the load cell 17. Additionally or alternatively, the data analysis device 10 may be configured to generate the desired estimate(s) and/or process control data 64 directly from the recorded changes in load.

Figure 6:
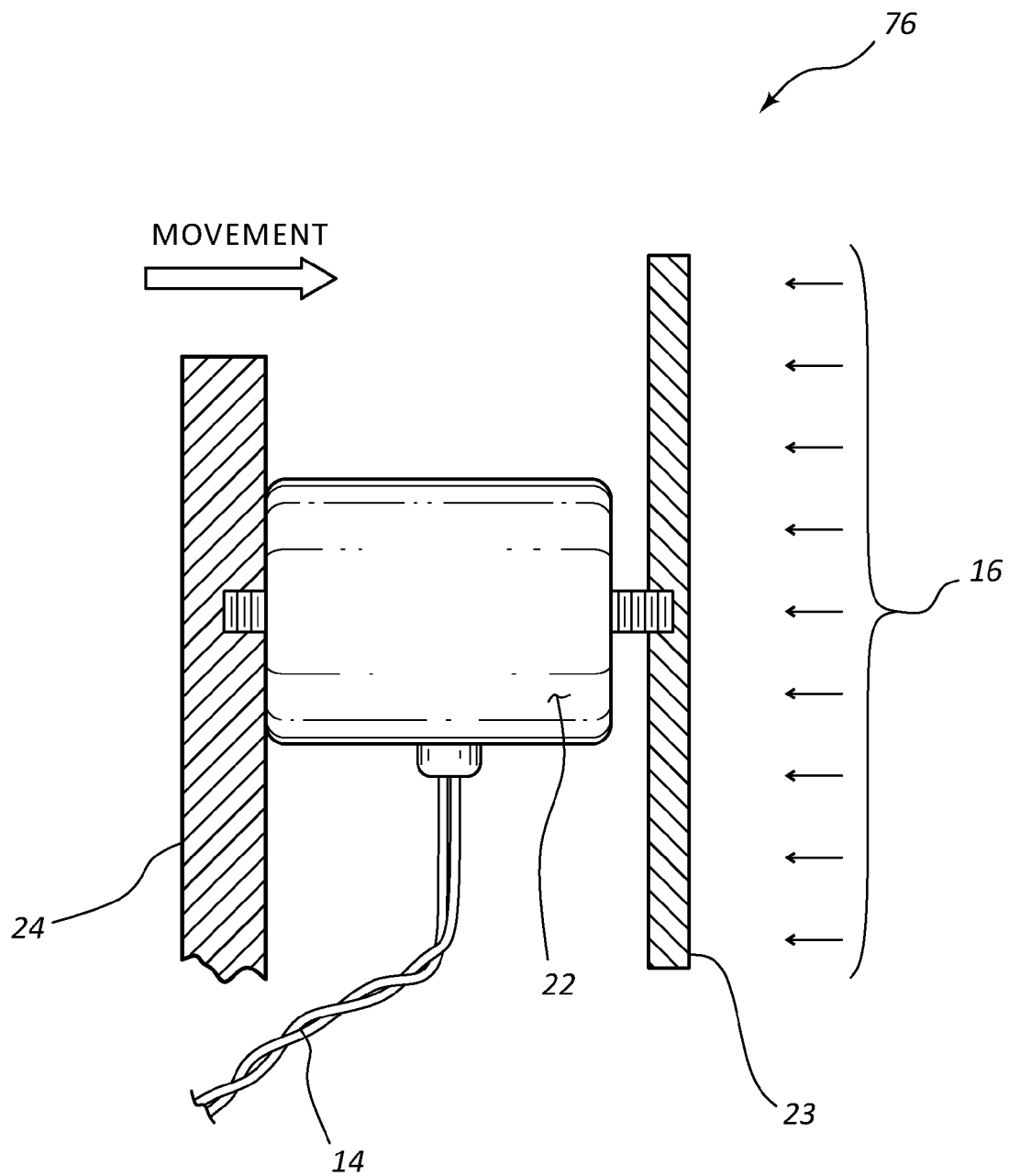
FIG. 6 is a side elevation view of a sensor similar to FIG. 5, without the protective housing.

Referring to FIG. 6, a side elevation view illustrates a sensor 76 similar to the sensor 74 of FIG. 5, without the protective housing 18. In the sensor 76, the load cell 22 itself may be watertight and may be used without further environmental protection. As in the sensor 74 of FIG. 5, the output signal response characteristics of the sensor 76 can be changed by adjusting the frontal area of the probe 23. Increasing the frontal area of the probe 23 may strengthen the output signal from the sensor 76, while reducing the frontal area of the probe 23 may reduce the output signal.

In this embodiment, the load cell 22 may be attached to a structure 24 that moves relative to the viscous material. The probe 23 may be attached directly to the load cell 22 without the need for an intermediate shaft such as the shaft 19 of FIG. 5. Movement of structure 24 through the viscous material 3 may create a viscous pressure 16 on the probe 23, resulting in a force sensed by the load cell 17.

Figure 7A:
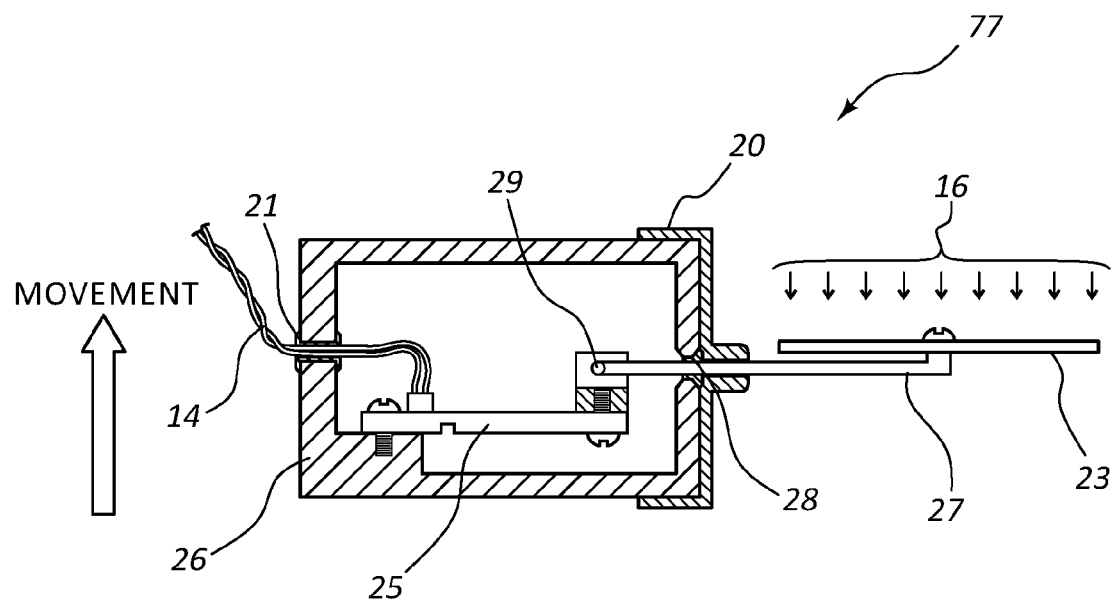
FIG. 7A is a side elevation view of a sensor according to another embodiment of the invention, with a beam type load cell and a lever arm arrangement that transmits force to the load cell for measurement.
Figure 7B:
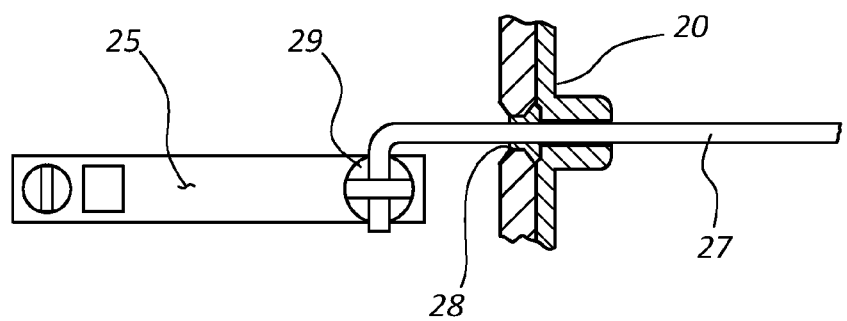
FIG. 7B is a detail view of the lever arm of the sensor of FIG. 7A.

Referring to FIGS. 7A and 7B, these side elevation and detail views illustrate a sensor 77 according to another embodiment of the invention. The illustrated embodiment of the sensor 77 includes a beam type load cell 25 and a lever arm arrangement that transmits force to the beam type load cell 25 for measurement. The sensor 77 may have a protective housing 26 within which the beam type load cell 25 is mounted. This embodiment differs from that of FIG. 5 in that the viscous pressure 16 generated by motion of the probe 23 through the viscous material 3 may be transmitted to the beam type load cell 25 through a lever arm formed by a shaft 27 coupled to the protective housing 26 such that the shaft 27 has a pivot point 28 proximate the location at which the shaft 27 passes through the protective housing 26. This lever arm arrangement may allow the magnitude of the force measured at the beam type load cell 25 to be adjusted by changing the ratio of the lengths of shaft 27 on either side of the pivot point 28. The resulting force from the viscous pressure 16 on the probe 23 may be transmitted to the beam type load cell 25 through the shaft 27 as the shaft 27 pivots at the pivot point 28 on the protective housing 26. The shaft 27 may also pivot at a point 29 at the end of the beam type load cell 25. The entire beam type load cell 25 may be protected from the viscous material 3 by the protective housing 26 and by an elastomeric membrane 20 that provides a flexible, watertight joint between the protective housing 26 and the shaft 27.

The beam type load cell 25 may be any of the load cell types listed above. According to one example, the beam type load cell 25 may include a beam with geometry, such as a notch, that facilitates bending. A strain gauge may be secured to the beam to measure strain in the beam in a manner similar to that of the strain gauges 7 of the sensor 72 of FIGS. 1-3B.

Figure 8A:
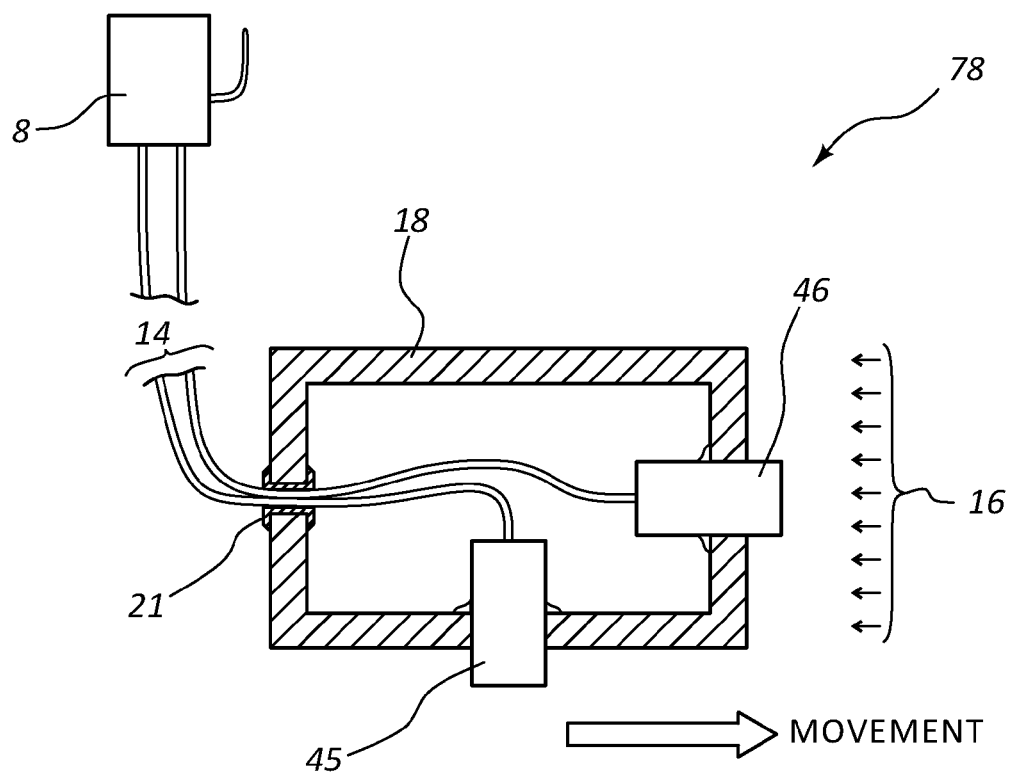
FIG. 8A is a top view of a sensor according to another embodiment of the invention, with load cells in the form of pressure detectors.
Figure 8B:
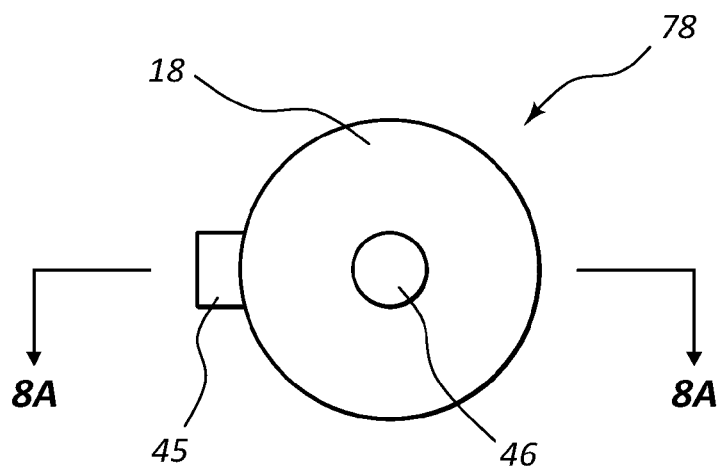
FIG. 8B is a front elevation view of the sensor of FIG. 8A.

Referring to FIGS. 8A and 8B, top and front elevation views illustrate a sensor 78 according to another embodiment of the invention, with load cells in the form of a first pressure detector 45 and a second pressure detector 46. In the sensor 78, viscous pressure 16, generated by moving the sensor 78 through the viscous material 3, may be measured through the use of a first pressure detector 45 and a second pressure detector 46. The first pressure detector 45 and the second pressure detector 46 may be mounted in a protective housing 18 that is watertight. Thus, the first pressure detector 45 and the second pressure detector 46 may be protected from the viscous material 3.

The sensor 78 may be submerged some depth in the viscous material 3. The first pressure detector 45 may be mounted generally at 90 degrees to the direction of movement of the sensor 78 through the viscous material 3. Thus, the first pressure detector 45 may detect only hydrostatic pressure from being submerged in the viscous material 3. Conversely, the second pressure detector 46 may be mounted parallel to the direction of movement of the sensor 78 through the viscous material 3. Thus, the second pressure detector 46 may sense the hydrostatic pressure of being submerged in the viscous material 3 plus the viscous pressure 16 generated by movement of the sensor 78 through the viscous material 3. If the viscous pressure 16 is the property of the viscous material 3 that is to be estimated, it may be obtained by subtracting the magnitude of the pressure detected by the first pressure detector 45 from the magnitude of the pressure detected by the second pressure detector 46.

Advantageously, the sensor 78 may also be used to obtain estimates of other properties of the viscous material 3. For example, the hydrostatic pressure of the viscous material 3 at the depth to which the sensor 78 is submerged may be obtained directly from the load data 62 (illustrated in FIG. 4) generated by the first pressure detector 45.

As in previous embodiments, electrical wires 14 may communicate the load data 62 from the first pressure detector 45 and the second pressure detector 46 to the wireless transceiver 8. The electrical wires 14 may go through an opening 21 in the protective housing 18, which may be made watertight by filling it with a commercially available potting compound that adheres to the electrical wires 14 and the protective housing 18.

In alternative embodiments (not shown), the first pressure detector 45 and the second pressure detector 46 may easily be replaced by a single differential pressure sensing instrument mounted inside a housing such as the protective housing 18 and having pressure taps at the same locations as the first pressure detector 45 and the second pressure detector 46. Such a differential pressure sensing instrument may, for example, have a membrane that maintains a pressure differential between two portions of the housing. One portion of the housing may receive pressure from alongside the housing, like the first pressure detector 45, and another portion of the housing may receive pressure from the leading end of the housing, like the second pressure detector 46. A pressure detector, strain gauge or other load cell may be positioned to measure the pressure differential between the two portions of the housing. Thus, the magnitude of the viscous pressure 16 may effectively be measured with a single load cell. Such a load cell may not then directly provide a measure of the hydrostatic pressure of the viscous material 3 surrounding the sensor.

Figure 9A:
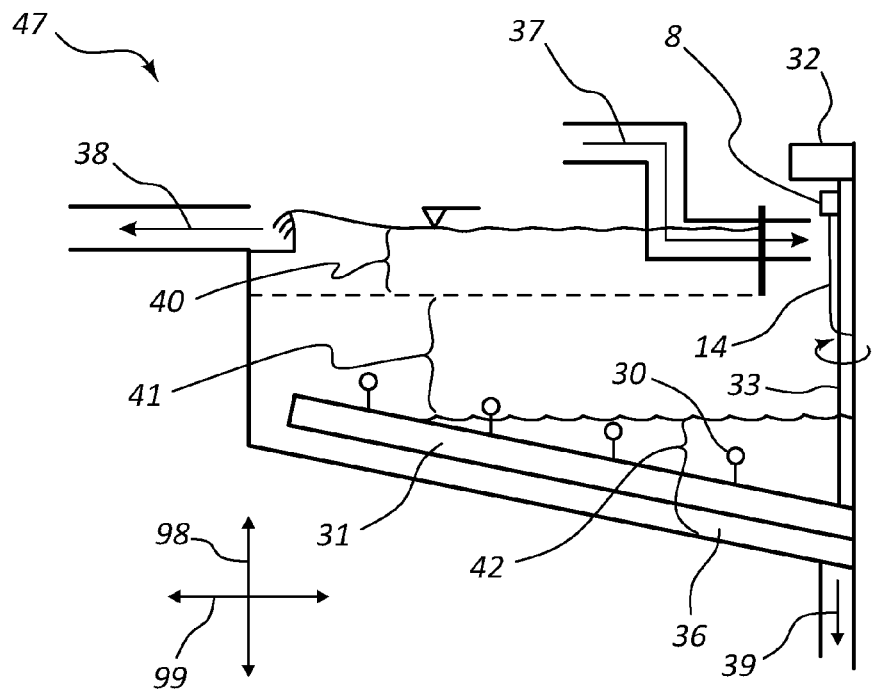
FIG. 9A is a side elevation, section view of a container of viscous material in the form of a shallow bed thickener, including multiple sensors attached to the thickener mechanism mechanically configured to rotate.

Referring to FIG. 9A, a side elevation, section view illustrates a container of viscous material 3 in the form of a shallow bed thickener 47, including multiple sensors 30 attached to a thickener mechanism mechanically configured to rotate 31. The sensors 30 may be of any of the types disclosed in connection with the previous Figures. In this embodiment, the sensors 30 may be arranged generally horizontally along the thickener mechanism mechanically configured to rotate 31. The thickener mechanism 31 may be powered by a thickener drive 32 through a drive shaft 33 or cage connecting the thickener mechanism 31 to the thickener drive 32. This rotation may provide a convenient method of moving the sensors 30 through the contents of the shallow bed thickener 47, generating a viscous pressure 16 and resulting force on the probes of the sensors 30. The sensors 30 may be connected to the wireless transceiver 8 via electrical wires 14, as in previous embodiments. The electrical wires 14 may extend along the drive shaft 33.

The shallow bed thickener 47 may include a tank 36 that contains the viscous material 3. The tank 36 may be fed by a feed stream 37 containing liquid and solids. The feed stream 37 may be a slurry. Overflow of clarified liquid 38 may leave the shallow bed thickener 47 near the top of the tank 36, and underflow 39 of concentrated solids may leave the shallow bed thickener 47 near the bottom of the tank 36. The viscous material 3 within the shallow bed thickener 47 may be made up of zones having different viscosities. The clarified liquid zone 40 will generally have very low viscosity. Below this is the settling zone 41, having higher viscosity than the zone above. The solids compaction zone 42, having the highest viscosity of the viscous material 3 inside the shallow bed thickener 47, is at the bottom of the tank 36.

The shallow bed thickener 47 and the member mechanically configured to rotate (i.e., the drive shaft 33) may have an axial dimension 98 parallel to the drive shaft 33, and a radial dimension 99 perpendicular to the axial dimension 98. When the shallow bed thickener 47 is oriented as in FIG. 9A, the axial dimension 98 may be a vertical dimension, and the radial dimension 99 may be a horizontal dimension. The axial dimension 98 and the radial dimension 99 are applicable to any embodiment in which a sensor 30 is secured to a member mechanically configured to rotate, which may be the drive shaft of a thickener mechanism, (the drive shaft 33 of the thickener mechanism 31 of FIG. 9A), or a dedicated member mechanically configured to rotate that is used for the sole purpose of moving sensors 30 through the viscous material 3, as will be shown and described in connection with FIGS. 10A and 10B.

With multiple sensors 30 arranged with some vertical offset, as is provided by the angle of the thickener mechanism 31 in FIG. 9A, it is possible to analyze the load data 62 from the sensors 30 and determine the approximate location of the interface between zones as well as the degree of compaction in the bed. It may be particularly desirable to determine the location of the interface between the settling zone 41 and the solids compaction zone 42.

Figure 9B:
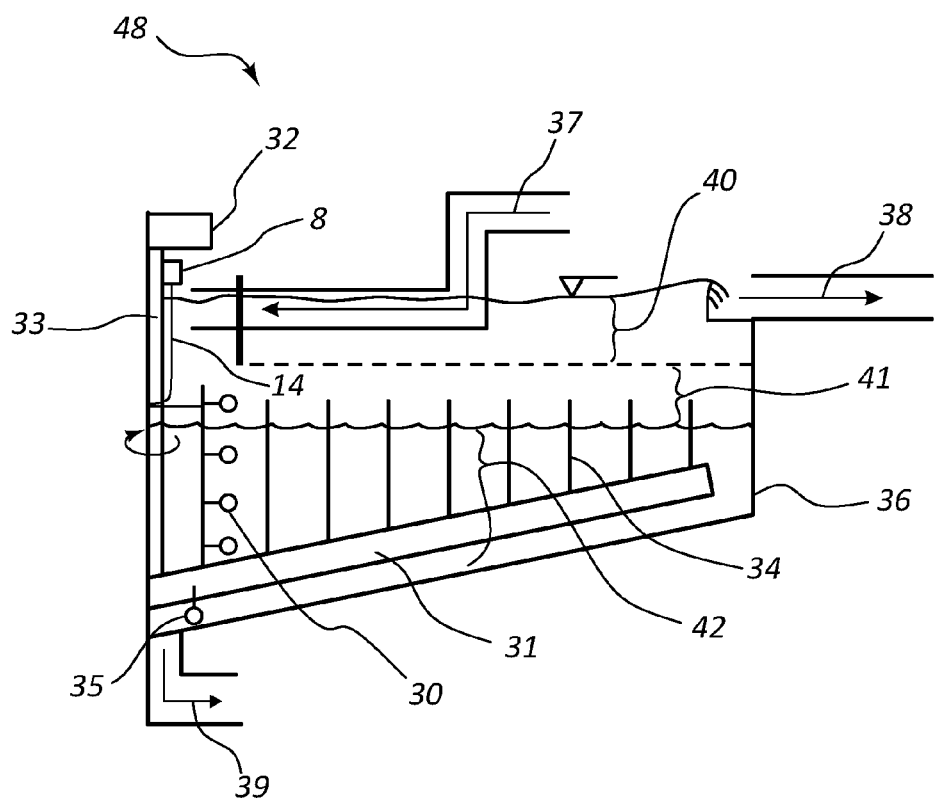
FIG. 9B is a side elevation, section view of a container of viscous material in the form of a deep bed thickener, including multiple sensors attached to the thickener mechanism mechanically configured to rotate.

Referring to FIG. 9B, a side elevation, section view illustrates a container of viscous material 3 in the form of a deep bed thickener 48, including multiple sensors 30 attached to the thickener mechanism mechanically configured to rotate 31. The deep bed thickener 48 may have vertical members in the form of pickets 34 extending upward from the thickener mechanism mechanically configured to rotate 31. The pickets 34 may be used to aid in the process of releasing liquid from the mud bed of the viscous material 3. These pickets 34 may provide a convenient mounting for sensors 30 arranged vertically. Electrical wires 14 may again connect the sensors 30 to a wireless transceiver 8 mounted above the contents of the deep bed thickener 48. The wireless transceiver 8 may be mounted on the drive shaft 33 or on an extension of a picket 34 with the electrical wires 14 being routed along the structure of the mechanism. In alternative embodiments, the wireless transceiver 8 may be integral to or in close proximity to each sensor 30.

A single sensor 35 could be placed near the center and bottom of the tank 36 of the deep bed thickener 48. In this case, the load data 62 (illustrated in FIG. 4) from the sensor 35 may provide a measurement of the underflow rheology near the thickener discharge, thus making it possible to determine whether the underflow 39 is acceptable for use in downstream processes. This information can be a valuable tool to predict and control thickener operation so as to produce acceptable underflow 39 more consistently than was previously possible before this invention. This sensor 35 could be used independently of or in addition to other sensors described in this application.

Figure 10A:
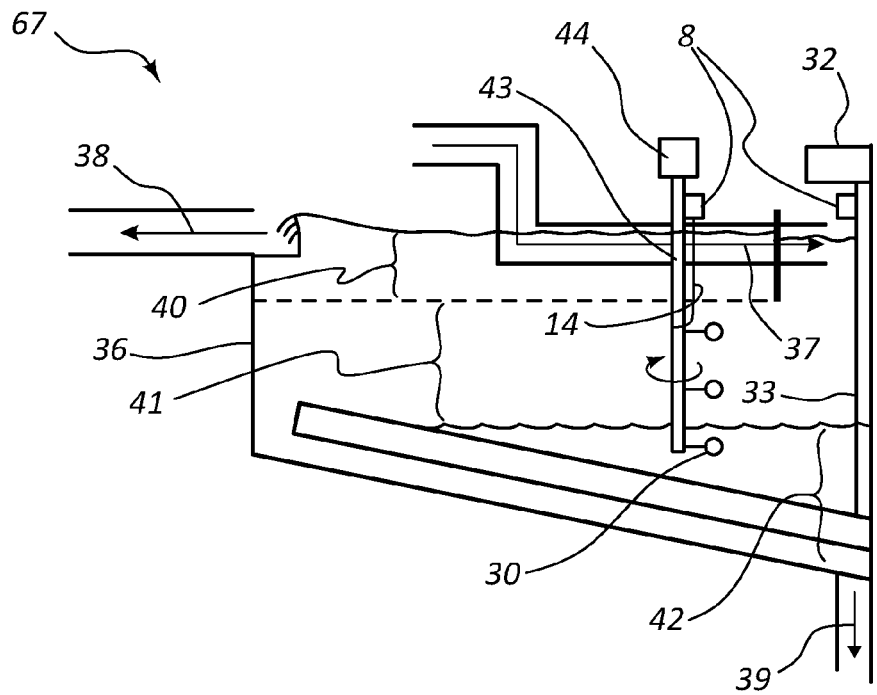
FIG. 10A is a side elevation, section view of a container of viscous material in the form of a shallow bed thickener, including multiple sensors attached to a shaft mechanically configured to rotate separate from the thickener mechanism.

Referring to FIG. 10A, a side elevation, section view illustrates a container of viscous material 3 in the form of a shallow bed thickener 67, including multiple sensors 30 attached to a shaft mechanically configured to rotate 43 separate from the thickener mechanism mechanically configured to rotate. 31. As in FIGS. 9A and 9B, the sensors 30 may include any of the types described previously. The sensors 30 on the shaft mechanically configured to rotate 43 may be generally vertical, and may also be generally independent of the thickener mechanism mechanically configured to rotate 31. The shaft mechanically configured to rotate 43 may be powered by any of a variety of mechanisms, including an electric gear motor 44 mounted to the bridge of the thickener mechanism mechanically configured to rotate 31. Electrical wires 14 from the sensors 30 may connect to the wireless transceiver 8, which may be located on the shaft mechanically configured to rotate 43 above the contents of the shallow bed thickener 67.

Figure 10B:
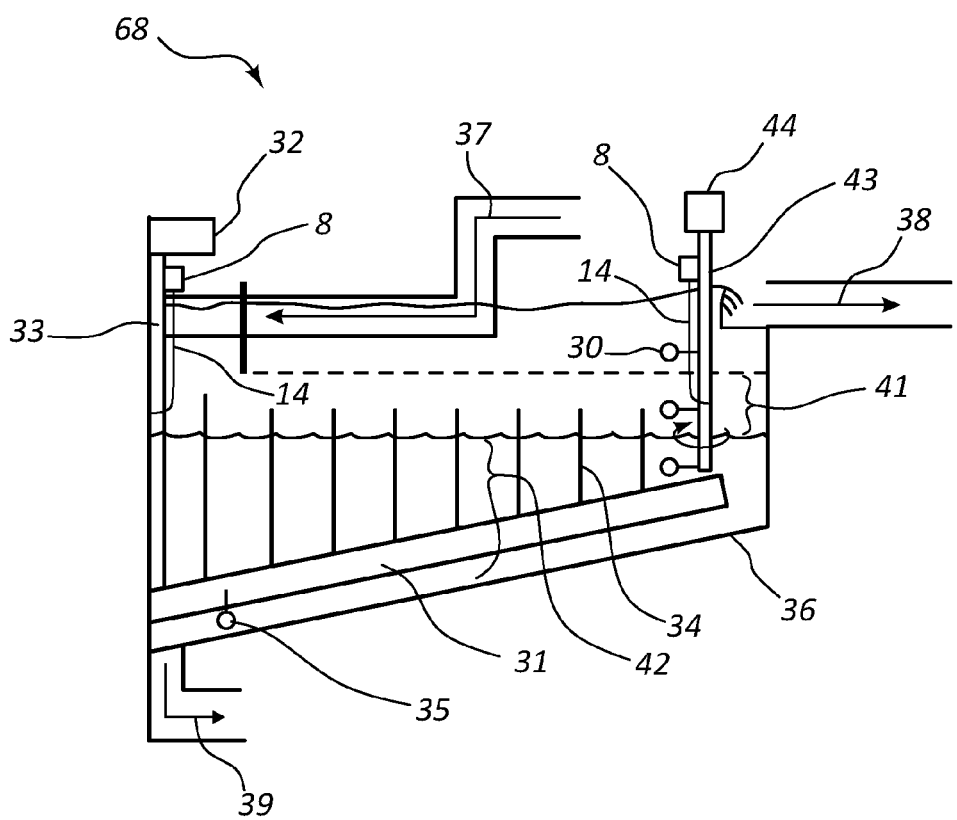
FIG. 10B is a side elevation, section view of a container of viscous material in the form of a deep bed thickener, including multiple sensors attached to a shaft mechanically configured to rotate independent from the thickener mechanism.

Referring to FIG. 10B, a side elevation, section view illustrates a container of viscous material 3 in the form of a deep bed thickener 68, including multiple sensors 30 attached to a shaft mechanically configured to rotate 43 independent from the thickener mechanism mechanically configured to rotate 31. Like the deep bed thickener 48 of FIG. 9B, the deep bed thickener 68 of FIG. 10B may have a relatively deep solids compaction zone 42. In this embodiment, the shaft mechanically configured to rotate 43 and sensors 30 may advantageously be located where they do not interfere with the thickener mechanism mechanically configured to rotate 31 and especially the pickets 34 and their support structures.

Data from any of the sensors 30 described previously can be collected, stored and analyzed to determine the approximate location of the interface between the settling zone 41 and the solids compaction zone 42, if the sensors 30 are positioned in a vertical arrangement. As in other embodiments, the load data 62, process control data 64, and/or any other applicable operational data may be dependent on the number of sensors 30 and the spacing between the sensors 30. Load data 62 from the sensors 30 may indicate strain, pressure, differential pressure, pressure change, or any other characteristic that can be measured by a load cell, depending on the type of load cell used. The load data 62 may, in one embodiment, be converted to more common units, such as yield stress of the viscous material 3, in Pascal, by signal conditioning hardware and/or software using the appropriate sensor geometry. Usage of more common units may facilitate relating the physical properties of the viscous material 3 to the load data 62 received.

In some embodiments, a single sensor 30 can be used in cases where a thickener is designed to operate at only one bed level. In such a case, the sensor 30 may be located in the tank of the thickener at the intended bed level (i.e., at the intended location of the interface between the settling zone 41 and the solids compaction zone 42). In operation, the solids compaction zone 42 (the "bed") could be built inside the tank. As the interface level rises during the initial stages of operation, the sensor 30 would yield load data 62 close to zero viscous pressure because of the low resistance encountered by the sensor 30 as it moves through the free settling solids. As the interface level approaches the sensor 30, the load data 62 may start to rise above zero viscous pressure. Because the interface level is not a distinct line, but a gradient, the viscous pressure 16 indicated by the load data 62 may continue to increase as the solids particles become more concentrated. When the measured viscous pressure 16 reaches a preset value, this may indicate that the interface has risen to the level of the sensor 30.

The preset value is dependent on the characteristics of viscous material 3 being processed and the type of thickener. With a simple calibration procedure, performed during startup of the instrument, manual measurements of the interface level can be correlated to the load data 62 and the proper signal magnitude can be selected to define the location of the mud bed interface. This may be called the set point output signal. Load data 62 indicating zero viscous pressure may indicate that the interface is some distance below the sensor 30. Load data 62 indicating viscous pressure above zero, but below the set point value, may indicate that the bed level is approaching the sensor 30. An output signal above the set point value may indicate that the actual interface level is above the sensor 30. The magnitude of the difference between the viscous pressure 16 provided by the load data 62 and the set point value may provide some indication of how far above the sensor 30 the actual interface is located.

A single sensor 30 could be used to control the mud bed level in a thickener by using it in an automated control system to adjust the underflow withdrawal rate so the output signal from the sensor 30 is maintained in a range of perhaps 5 Pascal on either side of the set point value.

In some embodiments, two or more sensors 30 can be arranged vertically inside a thickener to provide the ability to operate the thickener at different interface levels or to provide additional data to better define the location of the bed level interface. An example of three sensors 30 arranged vertically inside a thickener is useful to illustrate the operating principles. Assume these sensors 30 are identified as sensor 1, sensor 2 and sensor 3 and are spaced, for example, 1 meter apart. The lowest sensor 30 is sensor 1 and is located at the minimum operating level (i.e., the minimum desirable interface level). Sensor 2 is located 1 meter above sensor 1, at the normally expected interface level. Sensor 3 is located 1 meter above sensor 2, at the maximum design interface level. The sensors 30 and/or the data analysis device 10 may be calibrated to the operating process conditions and a set point value of 15 Pascal may be identified as representing the output signal at the mud bed interface. The thickener could be controlled to any of the bed levels at which sensors 30 are located by using the same procedures as described in the discussion above relative to use of a single sensor 30. However, because additional sensors 30 provide additional data, this information can be used to provide even more operational flexibility and precision in ascertaining viscosity characteristics within the viscous material 3.

If the sensor 2 provides an output signal equal to the set point value of 15 Pascal and sensor 1 is producing an output signal of 40 Pascal, the gradient between the two sensors is 25 Pascal. With 1 meter spacing between sensors, this provides an average of 0.25 Pascal per centimeter. This average assumes a linear relationship between yield stress and vertical position. Although this may not be strictly accurate, it is a reasonable estimate over a 1 meter vertical span and provides a close enough estimate for purposes of controlling a thickener. Having determined this gradient, it is now possible to operate the thickener at any desired bed level between sensor 1 and 3.

For example, the operator may wish to operate with an interface level halfway between sensors 2 and 3 (50 centimeters above the current bed level which is located at sensor 2). With the gradient of 0.25 Pascal per centimeter determined and the new, desired interface height above sensor 2 of 50 centimeters, a new set point for sensor 2 can be calculated to be (50×0.25)+15=27.5. This new set point for sensor 2 would be input into the control system. Underflow may be reduced, allowing the interface level to rise until the signal from sensor 2 reaches the new set point of 27.5 Pascal.

In other embodiments, more sensors may be used. The use of additional sensors may allow even more sophisticated computation of the gradient between sensors and thus more precision when operating at bed level interfaces between sensors.

In one embodiment, in addition to or in the alternative to the use of one or more vertically oriented sensors, multiple sensors may be oriented horizontally. One purpose of this sensor arrangement is to check for unusual operating conditions inside a thickener. Such unusual operating conditions may arise from phenomena occurring along a horizontal dimension. In theory, at any level inside a deep bed thickener, the compaction solids zone should have very similar physical properties. If there are significant differences between horizontally displaced sensors, this may be an indication of operational problems that require corrective action, such as alteration of flocculant input. Some examples of such problems include, for example: islands, which are regions near the bottom of the thickener having high viscosity surrounded by viscous material 3 of lower viscosity; a rotatable bed, in which a sizable volume of the compaction solids zone rotates with the thickener mechanism 31; a rat hole, also known as a short circuit in the center, which is a region of low viscosity viscous material 3 in the center of the thickener surrounded by higher viscosity viscous material 3; and a short circuit at the wall, which is a region of low viscosity viscous material 3 near the tank wall and floor of the thickener with higher viscosity material elsewhere in the thickener.

Figure 11:
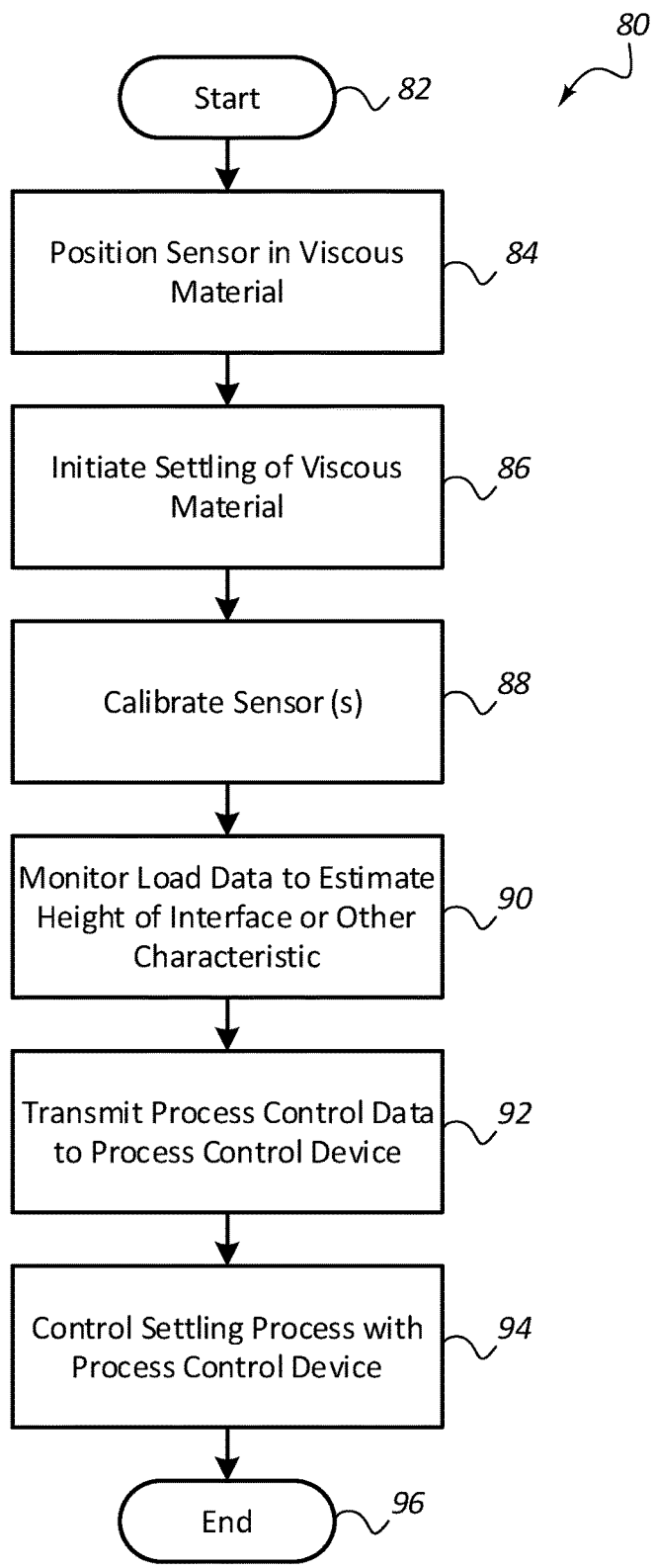
FIG. 11 is a flowchart diagram illustrating one method of sensing the viscosity characteristics of a viscous material, according to one embodiment of the invention.

Referring to FIG. 11, a flowchart diagram illustrates a generalized method 80 of sensing the viscosity characteristics of a viscous material 3, according to one embodiment of the invention. The method 80 may start 82 with a step 84, in which the one or more sensors 30 are positioned, submerged, or at least partially submerged or disposed within the viscous material 3. Then, in a step 86, settling of the viscous material 3 may be initiated, for example, by receiving the feed stream 37, adding flocculant, and/or operating the thickener mechanism 31. As the settling process is carried out, the method 80 may proceed to a step 88 in which the one or more sensors 30 are calibrated, for example, by manually measuring the depth of the interface between the settling zone 41 and the compaction solids zone 42, and comparing the measured depth to the load data 62 received from the one or more sensors 30.

Once the one or more sensors 30 have been properly calibrated, the method 80 may proceed to a step 90 in which the load data 62 is monitored to estimate one or more characteristics of the viscous material 3, such as viscous pressure, hydrostatic pressure, interface height, and/or other characteristics. This may be carried out by the data analysis device 10. Then, in a step 92, the process control data 64 may be transmitted to the process control device 58. The process control device 58 may then, in a step 94, utilize the process control data 64 to control one or more aspects of the settling process. Thereafter, the method 80 may conclude 96.

It is understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Figure 12:
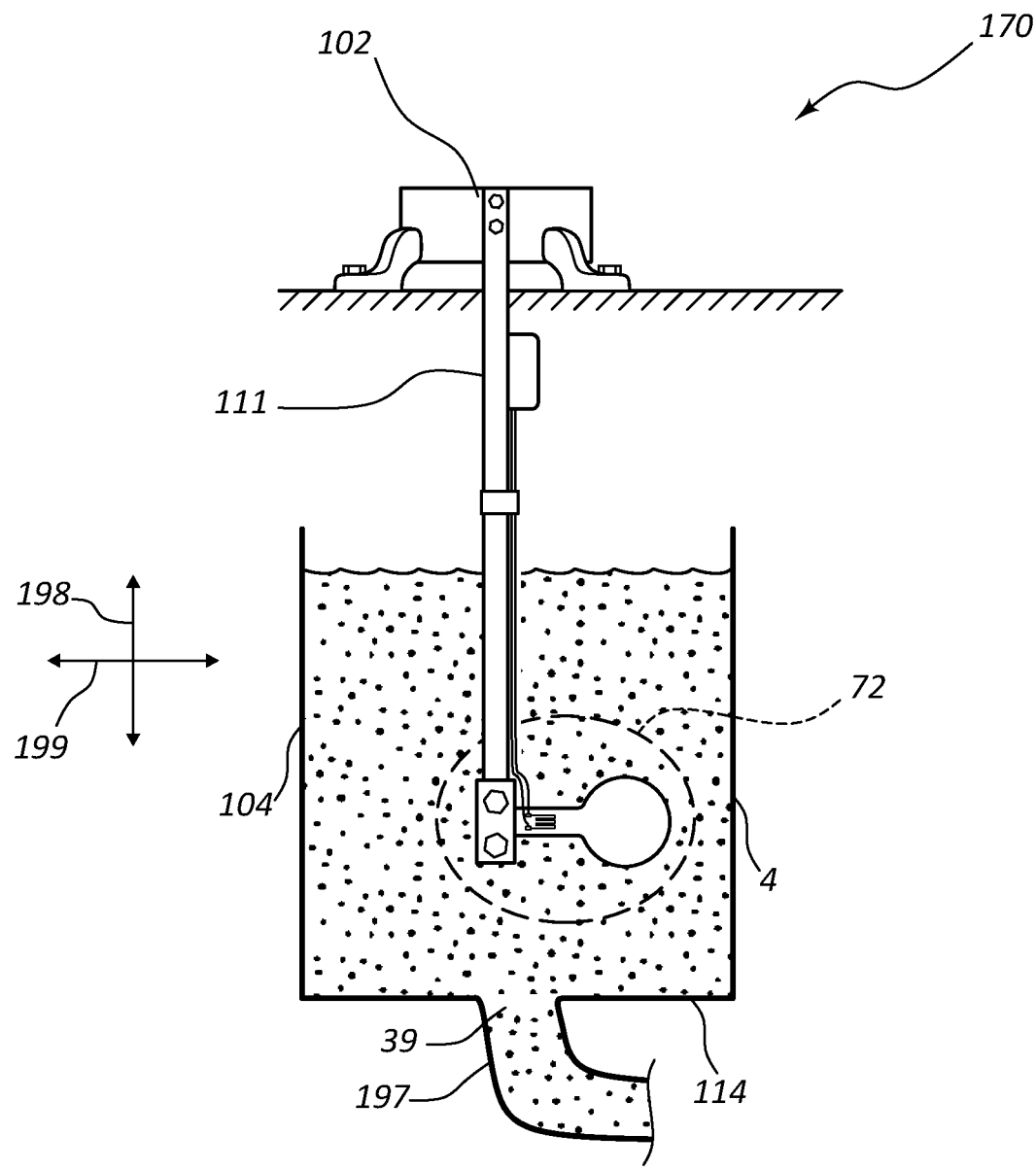
FIG. 12 is a side elevation, section view of an alternative embodiment of apparatus for determining one or more viscosity characteristics of a viscous material.

In connection the previously disclosed embodiments, such as the embodiment of FIG. 1, the shaft 1 mechanically configured to rotate. A shaft mechanically configured to rotate 1, however, comprises only one type of mounting structure 1, to which a sensor 72 may be secured. As explained above, such a shaft 1 may rotate to impart relative motion between the sensor 72 and the viscous material 3, enabling the detection or sensing of one or more viscosity characteristics of the viscous material 3. Referring now to FIG. 12, one embodiment of the apparatus 170 may include a mounting structure 111 that is stationary or not mechanically configured to rotate. As illustrated in FIG. 12, the shaft or mounting structure 111 may be secured to a base 102. In such an embodiment, force may be applied to the sensor 72 as a result of movement of the viscous material 3 relative to a sensor 72 secured to the mounting structure 111.

A stationary mounting structure could be embodied in a number of different ways. For example, the walls 104 and floor 114 of the container 4 may comprise a stationary mounting structure, to which one or more sensors 72 may be secured. An array of sensors 72 along a vertical dimension 198 and/or a horizontal dimension 199 of the viscous material 3 may also be used when a stationary mounting structure is employed. In addition and/or alternatively, an array of sensors 72 may be distributed along a pathway through which the viscous material 3 passes. In one embodiment, a sensor 72 may be positioned adjacent to an output port 197 to determine the rheological properties of the underflow 39.

The vertical dimension 198 of the viscous material 3 is generally parallel to the pull of gravity. The horizontal dimension 199 is perpendicular to the vertical dimension 198.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the scope of the disclosure. For example, in one embodiment, the member mechanically configured to rotate or shaft 1 may be omitted where the viscous material 3 flows in relation to a relatively stationary sensor 30, as discussed above in connection with FIG. 12. Further, each of the sensors 30, 35, 72, 74, 76, 77, 78 disclosed above may be used alone or in combination with other types of sensors 30, 35, 72, 74, 76, 77, 78 in various embodiments of the disclosed systems and apparatuses. Thus, the present disclosure is not intended to be limited to the aspects shown herein but is to be accorded the widest scope consistent with the principles and novel features disclosed.

What is claimed is:

1. An apparatus for sensing differences in viscosity within a viscous material in a container, comprising:

a member mechanically configured to rotate within the container;

a first arm secured to the member mechanically configured to rotate and extending from the member mechanically configured to rotate;

a first load cell mechanically coupled to the first arm to detect a first load applied to the first arm and to produce first load data indicative of the first load, the first arm passing through a first region within the container during a complete revolution of the member mechanically configured to rotate;

a second arm secured to the member mechanically configured to rotate and extending from the member mechanically configured to rotate, the second arm passing through a second region within the container during the complete revolution of the member mechanically configured to rotate, the first region being offset from the second region;

a second load cell mechanically coupled to the second arm to detect a second load applied to the second arm and to produce second load data indicative of the second load; and a data analysis device electrically coupled to the first load cell and to the second load cell, the data analysis device configured to receive the first load data indicative of viscosity of the viscous material in the first region and the second load data indicative of viscosity of the viscous material in the second region and to analyze differences between the first load data and the second load data to generate at least one estimate of a viscosity gradient of the viscous material in the container when at least one of the first and second arms is at least partially submerged within the viscous material.

2. The apparatus of claim 1, wherein the first and second arms comprise a first probe and a second probe, respectively, wherein the first and second probes are oriented generally perpendicular to a direction along which the first and second probes move through the viscous material in response to rotation of the first and second arms, wherein the first and second probes are mechanically coupled to the first and second load cells to transmit force to the first and second load cells in proportion to fluid drag on the first and second probes.

3. The apparatus of claim 1, wherein the first and second load cells are each selected from the group consisting of strain gauges, pressure detectors, piezoelectric load cells, vibrating wire load cells, and capacitive load cells.

4. The apparatus of claim 3, wherein the first load cell comprises a first strain gauge secured to the first arm to measure strain of the first arm incident to fluid drag induced by motion of the first arm through the viscous material when the first arm is submerged within the viscous material, and the second load cell comprises a second strain gauge secured to the second arm to measure strain of the second arm incident to fluid drag induced by motion of the second arm through the viscous material when the second arm is submerged within the viscous material.

5. The apparatus of claim 1, wherein the member mechanically configured to rotate comprises an axial dimension parallel to an axis of rotation of the member mechanically configured to rotate and a radial dimension perpendicular to the axial dimension, wherein the first arm is offset from the second arm along the radial dimension.

6. The apparatus of claim 1, wherein the member mechanically configured to rotate comprises an axial dimension parallel to an axis of rotation of the member mechanically configured to rotate and a radial dimension perpendicular to the axial dimension, wherein the first arm is offset from the second arm along the axial dimension.

7. The apparatus of claim 6, further comprising:
a third arm secured to the member mechanically configured to rotate and extending outward from the member mechanically configured to rotate, the third arm being offset from the second arm along the axial dimension;
a third load cell mechanically coupled to the third arm to detect a third load applied to the third arm;
a fourth arm secured to the member mechanically configured to rotate and extending outward from the member mechanically configured to rotate, the fourth arm being offset from the first arm along the radial dimension; and
a fourth load cell mechanically coupled to the fourth arm to detect a fourth load applied to the fourth arm.

8. The apparatus of claim 1, further comprising:
a rake extending from the member mechanically configured to rotate for raking the viscous material,
wherein the container comprises a gravity-driven sedimentation vessel shaped to hold the viscous material, wherein the member mechanically configured to rotate extends into the gravity-driven sedimentation vessel such that the rake is at least partially submerged in the viscous material when the viscous material is disposed within the gravity-driven sedimentation vessel.

9. The apparatus of claim 1, wherein the data analysis device analyzes the first load data and the second load data to ascertain a viscosity gradient indicative of a flow pattern of the viscous material within the container.

10. The apparatus of claim 9, wherein the flow pattern comprises an island, a rotatable bed, a rat hole or a short circuit at a wall.

11. The apparatus of claim 1, wherein the container comprises a gravity-driven sedimentation vessel shaped to receive an incoming slurry, the viscous material comprising at least a clarified liquid zone, a settling zone and a concentrated solids zone, the viscous material comprising a vertical dimension, and wherein the data analysis device is configured to ascertain an estimate of a location of interface between the settling zone and the concentrated solids zone along the vertical dimension based on the first load data and the second load data.

12. An apparatus for sensing viscosity of a viscous material within a gravity-driven sedimentation vessel shaped to hold the viscous material, the viscous material having at least a clarified liquid zone near a top of the viscous material from which clarified water can be removed, a concentrated solids zone near a bottom of the viscous material from which concentrated solids can be removed, the concentrated solids zone comprising a first viscosity, and a settling zone containing settling solids located between the clarified liquid zone and the concentrated solids zone, the settling zone comprising a second viscosity different from the first viscosity, the apparatus comprising:
a member mechanically configured to rotate within the gravity-driven sedimentation vessel;
a first arm secured to the member mechanically configured to rotate and extending from the member mechanically configured to rotate;
a first load cell mechanically coupled to the first arm to detect a first load applied to the first arm and to produce first load data indicative of the first load, the first arm passing through a first region within the vessel during a complete revolution of the member mechanically configured to rotate;

a second arm secured to the member mechanically configured to rotate and extending from the member mechanically configured to rotate, the second arm passing through a second region within the vessel during the complete revolution of the member mechanically configured to rotate, the first region being offset from the second region;

a second load cell mechanically coupled to the second arm to detect a second load applied to the second arm and to produce second load data indicative of the second load; and a data analysis device electrically coupled to the first load cell and to the second load cell, the data analysis device configured to receive the first load data indicative of viscosity of the viscous material in the first region and the second load data indicative of viscosity of the viscous material in the second region and to analyze differences between the first load data and the second load data to generate at least one estimate of a viscosity gradient of the viscous material in the vessel when at least one of the first and second arms is at least partially submerged within the viscous material.

13. The apparatus of claim 12, wherein the data analysis device is configured to ascertain changes in the viscosity gradient based on the first load data and the second load data.

14. The apparatus of claim 12, wherein the data analysis device is electrically coupled to at least one of the first load cell and the second load cell through a wireless communication link.

15. An apparatus for sensing differences in viscosity within a viscous material, comprising:
   a mounting structure;
   a first arm secured to the mounting structure and extending from the mounting structure;
   a first load cell mechanically coupled to the first arm to detect a first load applied to the first arm in a first region by relative movement between the first load cell and the viscous material and to produce first load data indicative of the first load;
   a second arm secured to the mounting structure and extending from the mounting structure, the second arm being offset from the first arm;
   a second load cell mechanically coupled to the second arm to detect a second load applied to the second arm in a second region by relative movement between the second load cell and the viscous material and to produce second load data indicative of the second load, the first region being offset from the second region; and
   a data analysis device electrically coupled to the first load cell and to the second load cell, the data analysis device configured to receive the first load data indicative of viscosity of the viscous material in the first region and the second load data indicative of viscosity of the viscous material in the second region and to analyze differences between the first load data and the second load data to generate at least one estimate of a viscosity gradient of the viscous material when at least one of the first and second arms is at least partially submerged within the viscous material.

16. The apparatus of claim 15, the mounting structure comprises a member mechanically configured to rotate.

17. The apparatus of claim 16, wherein the data analysis device analyzes the first load data and the second load data to ascertain a viscosity gradient indicative of a flow pattern of the viscous material, wherein the flow pattern comprises an island, a rotatable bed, a rat hole, or a short circuit at a wall.

18. An apparatus for sensing viscosity of a viscous material within a gravity-driven sedimentation vessel shaped to hold the viscous material, the viscous material having at least a clarified liquid zone near a top of the viscous material from which clarified water can be removed, a concentrated solids zone near a bottom of the viscous material from which concentrated solids can be removed, the concentrated solids zone comprising a first viscosity, and a settling zone containing settling solids located between the clarified liquid zone and the concentrated solids zone, the settling zone comprising a second viscosity different from the first viscosity, the apparatus comprising:
   a member mechanically configured to rotate extending into the viscous material;
   an arm secured to the member mechanically configured to rotate, the arm passing through a region during a single revolution of the member mechanically configured to rotate; and
   a load cell mechanically coupled to the arm to detect a load applied to the arm by relative movement between the load cell and the viscous material in at least one of the clarified liquid zone, the concentrated solids zone, and the settling zone and to produce load data indicative of viscosity of the viscous material in the region when the arm is at least partially disposed within the viscous material; and
   a data analysis device electrically coupled to the load cell, the data analysis device configured to receive the load data and to estimate, in real time, an actual bed level interface between the settling zone and the concentrated solids zone of the viscous material within the gravity-driven sedimentation vessel based on a comparison between the load data and a set point value, the set point value being generated during a calibration procedure, the set point value corresponding to a desired bed level interface, wherein a magnitude of a difference, if any, between the load data and the set point value is indicative of a magnitude of a difference between the actual bed level interface and the desired bed level interface, if any.

19. The apparatus of claim 18, wherein the data analysis device is configured to ascertain a location of the actual bed level interface between the settling zone and the concentrated solids zone along a vertical dimension of the viscous material based on the load data.

* * * * *